(12) United States Patent  
Staehle et al.

(10) Patent No.: US 7,470,702 B2
(45) Date of Patent: Dec. 30, 2008

(54) BENZIMIDAZOLES

(75) Inventors: Wolfgang Staehle, Ingelheim (DE); Hans-Peter Buchstaller, Griesheim (DE); Alfred Jonczyk, Darmstadt (DE); Wilfried Rautenberg, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/577,033

(22) PCT Filed: Oct. 14, 2004

(86) PCT No.: PCT/EP2004/011550

§ 371 (c)(1),
(2), (4) Date: Apr. 24, 2006

(87) PCT Pub. No.: WO2005/042520

PCT Pub. Date: May 12, 2005

(65) Prior Publication Data

US 2007/0066660 A1  Mar. 22, 2007

(30) Foreign Application Priority Data

Oct. 24, 2003  (DE)  ................. 103 49 587

(51) Int. Cl.
*A01N 43/40* (2006.01)
*A61K 31/435* (2006.01)
*C07D 213/00* (2006.01)

(52) U.S. Cl. .......................... 514/277; 546/1

(58) Field of Classification Search ............. None
See application file for complete search history.

(56) References Cited

FOREIGN PATENT DOCUMENTS

| FR | 2851563 | * | 8/2004 |
| GB | 1 171 904 | A | 11/1969 |
| JP | 60 213945 | A | 10/1985 |
| WO | WO 01/25238 | A | 12/2001 |
| WO | WO 02/44156 | A | 6/2002 |
| WO | WO 03/082272 | A | 9/2003 |
| WO | WO 03/074515 | A | 12/2003 |
| WO | WO 2004/085425 | A | 7/2004 |
| WO | WO2004085425 | * | 10/2004 |

OTHER PUBLICATIONS

Vippagunta et al. Advanced Drug Delivery Reviews, 2001, 48, 3-26.*
Campochiaro, P. Expert Opinion in Biological Therapy, 2004, 4(9), 1395-1402.*
Garin, Javier et al., Diheterocyclic compounds from dithiocarbamates and derivatives thereof. XP002317608, Database accession No. 1990:478244, Journal of Heterocyclic Chemistry 27(2), 221-6, Database Caplus Chemical Abstracts Service, Columbus, Ohio, US.
Yamamoto, Yoshitimo et al., "2-p-(Substituted aminio)anilinobenzimidazoles", XP002317609, Database accession No. 1980:111007 and JP 54 081271A, Jun. 28, 1979; Database Caplus Chemical Abstracts Service, Columbus, Ohio, US.
Tolea, Anica et al., "Dipolar cycloadditions of benzimidazole 3-oxides with aromatic diisocyanates", XP002317610, Database accession No. 1978:61742; Revistade Chimie 28(9), 823-5 Coden; Database Caplus Chemical Abstracts Service, Columbus, Ohio, US.

* cited by examiner

*Primary Examiner*—James O. Wilson
*Assistant Examiner*—Noble Jarrell
(74) *Attorney, Agent, or Firm*—Arent Fox LLP

(57) ABSTRACT

Novel compounds of the formula I in which $R^1$, $R^{1'}$, L, E, G, M, Q, U, $R^2$, m, p and q have the meanings indicated. Further, the compounds of formula I can be used as, for example, inhibitors of tyrosine kinases, for example TIE-2, and can be employed, for example, for the treatment of tumours or other diseases.

(I)

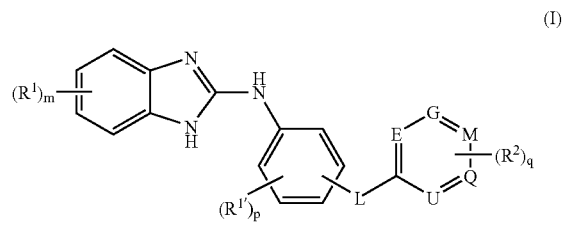

13 Claims, No Drawings

BENZIMIDAZOLES

BACKGROUND OF THE INVENTION

The invention had the object of finding novel compounds having valuable properties, in particular those which can be used for the preparation of medicaments.

The present invention relates to compounds in which the inhibition, regulation and/or modulation of kinase signal transduction, in particular tyrosine kinase and/or Raf kinase signal transduction, plays a role, furthermore to pharmaceutical compositions which comprise these compounds, and to the use of the compounds for the treatment of kinase-induced diseases.

Specifically, the present invention relates to compounds which inhibit, regulate and/or modulate tyrosine kinase signal transduction, to compositions which comprise these compounds, and to methods for the use thereof for the treatment of tyrosine kinase-induced diseases and conditions, such as angiogenesis, cancer, tumour growth, arteriosclerosis, age-induced macular degeneration, diabetic retinopathy, inflammatory diseases and the like, in mammals.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important factors in cell proliferation, carcinogenesis and cell differentiation.

Tyrosine kinases can be categorised as receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular.

Receptor-type tyrosine kinases consist of a multiplicity of transmembrane receptors with different biological activity. Thus, about 20 different subfamilies of receptor-type tyrosine kinases have been identified. One tyrosine kinase subfamily, known as the HER subfamily, consists of EGFR, HER2, HER3 and HER4. Ligands from this subfamily of receptors include epithelial growth factor, TGF-α, amphiregulin, HB-EGF, betacellulin and heregulin. Another subfamily of these receptor-type tyrosine kinases is the insulin subfamily, which includes INS-R, IGF-IR and IR-R. The PDGF subfamily includes the PDGF-α and -β receptors, CSFIR, c-kit and FLK-II. In addition, there is the FLK family, which consists of the kinase insert domain receptor (KDR), foetal liver kinase-1 (FLK-1), foetal liver kinase-4 (FLK-4) and fms tyrosine kinase-1 (flt-1). The PDGF and FLK families are usually discussed together due to the similarities between the two groups. For a detailed discussion of receptor-type tyrosine kinases, see the paper by Plowman et al., *DN & P* 7(6):334-339, 1994, which is hereby incorporated by way of reference.

Non-receptor-type tyrosine kinases likewise consist of a multiplicity of subfamilies, including Src, Frk, Btk, Csk, Abl, Zap70, Fes/Fps, Fak, Jak, Ack, and LIMK. Each of these subfamilies is further sub-divided into different receptors. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor-type tyrosine kinases, see the paper by Bolen *Oncogene,* 8:2025-2031 (1993), which is hereby incorporated by way of reference.

Both receptor-type tyrosine kinases and non-receptor-type tyrosine kinases are involved in cellular signalling pathways leading to various pathogenic conditions, including cancer, psoriasis and hyperimmune responses. It has been proposed that various receptor-type tyrosine kinases, and the growth factors binding to them, play a role in angiogenesis, although some may promote angiogenesis indirectly (Mustonen and Alitalo, *J. Cell Biol.* 129:895-898,1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11-15, 1993). VEGF and KDR are a ligand-receptor pair which plays a vital role in the proliferation of vascular endothelial cells and the formation and sprouting of blood vessels, referred to as vasculogenesis and angiogenesis respectively.

Angiogenesis is characterised by excessive activity of vascular endothelial growth factor (VEGF). VEGF actually consists of a family of ligands (Klagsburn and D'Amore, *Cytokine & Growth Factor Reviews* 7:259-270, 1996). VEGF binds the high affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be susceptible to the antiangiogenic effect of VEGF receptor antagonists (Kim et al., Nature 362, pp. 841-844, 1993).

Three PTK (protein tyrosine kinase) receptors for VEGFR have been identified: VEGFR-1 (Flt-1); VEGRF-2 (Flk-1 or KDR) and VEGFR-3 (Flt-4). VEGFR-2 is of particular interest.

Solid tumours can therefore be treated with tyrosine kinase inhibitors since these tumours depend on angiogenesis for the formation of the blood vessels that are necessary to support their growth. These solid tumours include monocytic leukaemia, brain, urogenital tract, lymphatic system, stomach, larynx and lung carcinoma, including lung adenocarcinoma and small cell lung carcinoma. Further examples include carcinomas in which overexpression or activation of Raf-activating oncogenes (for example, K-ras, erb-B) is observed. These carcinomas include pancreatic and breast carcinoma. Inhibitors of these tyrosine kinases are therefore suitable for the prevention and treatment of proliferative diseases caused by these enzymes.

The angiogenic activity of VEGF is not limited to tumours. VEGF accounts for the angiogenic activity produced in or near the retina in diabetic retinopathy. This vascular growth in the retina leads to visual degeneration culminating in blindness. Ocular VEGF mRNA and protein levels are elevated by conditions such as retinal vein occlusion in primates and decreased $pO_2$ level in mice that lead to neovascularisation. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

Expression of VEGF is also significantly increased in hypoxic regions of animal and human tumours adjacent to areas of necrosis. In addition, VEGF is upregulated by the expression of the oncogenes Ras, Raf, Src and mutant p53 (all of which are important in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activities. These monoclonal antibodies also inhibit the growth of typically less well vascularised human colon carcinomas in athymic mice and decrease the number of tumours arising from inoculated cells.

The expression of a VEGF-binding construct of Flk-1, Flt-1, the mouse KDR receptor homologue truncated to eliminate the cytoplasmic tyrosine kinase domains but retaining a membrane anchor, in viruses virtually stops the growth of a transplantable glioblastoma in mice, presumably by the dominant negative mechanism of heterodimer formation with membrane-spanning endothelial cell VEGF receptors. Embryonic stem cells, which normally grow as solid tumours in nude mice, do not produce detectable tumours if both VEGF alleles are knocked out. Taken together, these data indicate the role of VEGF in the growth of solid tumours. Inhibition of KDR or Flt-1 is involved in pathological angiogenesis, and these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp. 1-8, 1991).

Angiopoietin 1 (Ang1), a ligand for the endothelium-specific receptor-type tyrosine kinase TIE-2, is a novel angiogenic factor (Davis et al, Cell, 1996, 87:1161-1169; Partanen et al, Mol. Cell Biol., 12:1698-1707 (1992); U.S. Pat. Nos. 5,521,073; 5,879,672; 5,877,020; and 6,030,831). The acronym TIE stands for "tyrosine kinase with Ig and EGF homology domains". TIE is used for the identification of a class of receptor-type tyrosine kinases which are expressed exclusively in vascular endothelial cells and early haemopoietic cells. TIE receptor kinases are typically characterised by the presence of an EGF-like domain and an immunoglobulin (ig)-like domain which consists of extracellular fold units stabilised by disulfide bridge bonds between the chains (Partanen et al Curr. Topics Microbiol. Immunol., 1999, 237:159-172). In contrast to VEGF, which exerts its function during the early stages of vascular development, Ang1 and its receptor TIE-2 act during the later stages of vascular development, i.e. during vascular transformation (transformation relates to the formation of a vascular lumen) and maturing (Yancopoulos et al, Cell, 1998, 93:661-664; Peters, K. G., Circ. Res., 1998, 83(3):342-3; Suri et al, Cell 87, 1171-1180 (1996)).

Accordingly, it would be expected that inhibition of TIE-2 should interrupt the transformation and maturing of a new vascular system initiated by angiogenesis and should thus interrupt the angiogenesis process. Furthermore, inhibition at the kinase domain binding site of VEGFR-2 would block phosphorylation of tyrosine residues and serve to interrupt initiation of angiogenesis. It must therefore be assumed that inhibition of TIE-2 and/or VEGFR-2 should prevent tumour angiogenesis and serve to slow or completely eliminate tumour growth.

Accordingly, treatment of cancer and other diseases associated with inappropriate angiogenesis could be provided.

The present invention is directed to methods for the regulation, modulation or inhibition of TIE-2 for the prevention and/or treatment of diseases associated with unregulated or disturbed TIE-2 activity. In particular, the compounds according to the invention can also be employed in the treatment of certain forms of cancer. Furthermore, the compounds according to the invention can be used to provide additive or synergistic effects in certain existing cancer chemotherapies and/or can be used to restore the efficacy of certain existing cancer chemotherapies and radiotherapies.

The present invention is directed to methods for the regulation, modulation or inhibition of VEGFR-2 for the prevention and/or treatment of diseases associated with unregulated or disturbed VEGFR-2 activity.

The compounds according to the invention are preferably benzimidazolyl derivatives having TIE-2 and/or VEGFR-2 kinase activity.

The present invention furthermore relates to the compounds as inhibitors of Raf kinases.

Protein phosphorylation is a fundamental process for the regulation of cellular functions. The coordinated action of both protein kinases and phosphatases controls the degrees of phosphorylation and, hence, the activity of specific target proteins. One of the predominant roles of protein phosphorylation is in signal transduction, where extracellular signals are amplified and propagated by a cascade of protein phosphorylation and dephosphorylation events, for example in the $p21^{ras}$/Raf pathway.

The $p21^{ras}$ gene was discovered as an oncogene of the Harvey (H-Ras) and Kirsten (K-Ras) rat sarcoma viruses. In humans, characteristic mutations in the cellular Ras gene (c-Ras) have been associated with many different types of cancer. These mutant alleles, which render Ras constitutively active, have been shown to transform cells, such as, for example, the murine cell line NIH 3T3, in culture.

The $p21^{ras}$ as oncogene is a major contributor to the development and progression of human solid carcinomas and is mutated in 30% of all human carcinomas (Bolton et al. (1994) Ann. Rep. Med. Chem., 29, 165-74; Bos. (1989) Cancer Res., 49, 4682-9). In its normal, unmutated form, the Ras protein is a key element of the signal transduction cascade directed by growth factor receptors in almost all tissues (Avruch et al. (1994) Trends Biochem. Sci., 19, 279-83).

Biochemically, Ras is a guanine nucleotide binding protein, and cycling between a GTP-bound activated and a GDP-bound resting form is strictly controlled by Ras endogenous GTPase activity and other regulatory proteins. The Ras gene product binds to guanine triphosphate (GTP) and guanine diphosphate (GDP) and hydrolyses GTP to GDP. Ras is active in the GTP-bound state. In the Ras mutants in cancer cells, the endogenous GTPase activity is reduced and the protein consequently transmits constitutive growth signals to downstream effectors, such as, for example, the enzyme Raf kinase. This leads to the cancerous growth of the cells which carry these mutants (Magnuson et al. (1994) Semin. Cancer Biol., 5, 247-53). The Ras proto-oncogene requires a functionally intact C-Raf-1 proto-oncogene in order to transduce growth and differentiation signals initiated by receptor- and non-receptor-type tyrosine kinases in higher eukaryotes.

Activated Ras is necessary for the activation of the C-Raf-1 proto-oncogene, but the biochemical steps through which Ras activates the Raf-1 protein (Ser/Thr) kinase are now well characterised. It has been shown that inhibiting the effect of active Ras by inhibiting the Raf kinase signalling pathway by administration of deactivating antibodies to Raf kinase or by co-expression of dominant negative Raf kinase or dominant negative MEK (MAPKK), the substrate of Raf kinase, leads to reversion of transformed cells to the normal growth phenotype, see: Daum et al. (1994) Trends Biochem. Sci., 19, 474-80; Fridman et al. (1994) J Biol. Chem., 269, 30105-8. Kolch et al. (1991) Nature, 349, 426-28) and for a review Weinstein-Oppenheimer et al. Pharm. & Therap. (2000), 88, 229-279.

Similarly, inhibition of Raf kinase (by antisense oligodeoxynucleotides) has been correlated in vitro and in vivo with inhibition of the growth of a variety of human tumour types (Monia et al., Nat. Med. 1996, 2, 668-75).

Raf serine- and threonine-specific protein kinases are cytosolic enzymes that stimulate cell growth in a variety of cellular systems (Rapp, U. R., et al. (1988) in The Oncogene Handbook; T. Curran, E. P. Reddy and A. Skalka (eds.) Elsevier Science Publishers; The Netherlands, pp. 213-253; Rapp, U. R. et al. (1988) Cold Spring Harbor Sym. Quant. Biol. 53:173-184; Rapp, U. R. et al. (1990) Inv Curr. Top. Microbiol. Immunol. Potter and Melchers (eds.), Berlin, Springer-Verlag 166:129-139).

Three isozymes have been characterised:

C-Raf (also known as Raf-1, C-Raf-1, c-far-1 or c-raf1) (Bonner, T. I., et al. (1986) Nucleic Acids Res. 14:1009-1015). A-Raf (Beck, T. (1987) Nucleic Acids Res. 15:595-609), and B-Raf (Qkawa, S., et al. (1998) Mol. Cell. Biol. 8:2651-2654; Sithanandam, G. et al. (1990) Oncogene: 1775). These enzymes differ in their expression in various tissues. Raf-1 is expressed in all organs and in all cell lines that have been examined, and A- and B-Raf are expressed in urogenital and brain tissues respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal of or interference with an N-terminal negative regulatory domain of the protein (Heidecker, G., et al. (1990) Mol. Cell. Biol. 10:2503-2512; Rapp, U. R., et al.(1987) in Oncogenes and Cancer; S. A. Aaronson, J. Bishop, T. Sugimura, M. Terada, K. Toyoshima and P. K. Vogt (eds.) Japan Scientific Press, Tokyo). Microinjection into NIH 3T3 cells of oncogenically activated, but not wild-type, versions of the Raf protein prepared with *Escherichia coli* expression vectors results in morphological transformation and stimulates DNA synthesis (Rapp, U. R. et al. (1987) in Oncogenes and Cancer; S. A. Aaronson, J. Bishop, T. Sugimura, M. Terada, K. Toyoshima, and P. K. Vogt (eds.) Japan Scientific Press, Tokyo; Smith, M. R., et al. (1990) Mol. Cell. Biol. 10:3828-3833).

Consequently, activated Raf-1 is an intracellular activator of cell growth. Raf-1 protein serine kinase is a candidate for the downstream effector of mitogen signal transduction, since Raf oncogenes overcome growth arrest resulting from a block of cellular Ras activity due either to a cellular mutation (Ras revertant cells) or microinjection of anti-Ras antibodies (Rapp, U. R. et al. (1988) in The Oncogene Handbook, T. Curran, E. P. Reddy and A. Skalka (eds.), Elsevier Science Publishers; The Netherlands, pp. 213-253; Smith, M. (1986) Nature (London) 320:540-543).

C-Raf function is required for transformation by a variety of membrane-bound oncogenes and for growth stimulation by mitogens contained in serums (Smith, M. (1986) Nature (London) 320:540-543). Raf-1 protein serine kinase activity is regulated by mitogens via phosphorylation (Morrison, D. (1989) Cell 58:648-657), which also effects sub-cellular distribution (Olah, Z., et al. (1991) Exp. Brain Res. 84:403; Rapp, U. R. et al. (1988) Cold Spring Harbor Sym. Quant. Biol. 53:173-184. Raf-1 activating growth factors include platelet-derived growth factor (PDGF) (Morrison, D. (1988) Proc. Natl. Acad. Sci. USA 85:8855-8859), colony-stimulating factor (Baccarini, M., et al. (1990) EMBO J. 9:3649-3657), insulin (Blackshear, P. (1990) J. Biol. Chem. 265: 12115-12118), epidermal growth factor (EGF) (Morrison, R. (1988) Proc. Natl. Acad. Sci. USA 85:8855-8859), interleukin-2 (Turner, B. (1991) Proc. Natl. Acad. Sci. USA 88:1227) and interleukin-3 and granulocyte macrophage colony-stimulating factor (Carroll, M. (1990) J. Biol. Chem. 265:19812-19817).

After mitogen treatment of cells, the transiently activated Raf-1 protein serine kinase translocates to the perinuclear area and the nucleus (Olah, Z., et al. (1991) Exp. Brain Res. 84:403; Rapp, U. R. et al. (1988) Cold Spring Harbor Sym. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374) and Raf oncogenes activate transcription from Ap-I/PEA3-dependent promoters in transient transfection assays (Jamal, S., et al. (1990) Science 344:463-466; Kaibuchi, K., et al. (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. (1990) J. Biol. Chem. 265:12131-12134; Kovacina, K. (1990) J. Biol. Chem. 265:12115-12118; Morrison, D. (1988) Proc. Natl. Acad. Sci. USA 85:8855-8859; Siegel, J. (1990) J. Biol. Chem. 265:18472-18480; Turner, B. (1991) Proc. Natl. Acad. Sci. USA 88:1227). In each case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of conditions and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The identification of small compounds which specifically inhibit, regulate and/or modulate signal transduction of tyrosine kinases and/or Raf kinases is therefore desirable and an aim of the present invention.

It has been found that the compounds according to the invention and salts thereof have very valuable pharmacological properties while being well tolerated.

In particular, they exhibit tyrosine kinase inhibiting properties.

It has furthermore been found that the compounds according to the invention are inhibitors of the enzyme Raf kinase. Since the enzyme is a downstream effector of $p21^{ras}$, the inhibitors prove to be suitable in pharmaceutical compositions for use in human or veterinary medicine where inhibition of the Raf kinase pathway is indicated, for example in the treatment of tumours and/or cancerous cell growth mediated by Raf kinase. In particular, the compounds are suitable for the treatment of human and animal solid cancers, for example murine cancer, since the progression of these cancers is dependent upon the Ras protein signal transduction cascade and therefore susceptible to treatment by interruption of the cascade, i.e. by inhibiting Raf kinase. Accordingly, the compound according to the invention or a pharmaceutically acceptable salt thereof is administered for the treatment of diseases mediated by the Raf kinase pathway, especially cancer, including solid cancers, such as, for example, carcinomas (for example of the lungs, pancreas, thyroid, bladder or colon), myeloid diseases (for example myeloid leukaemia) or adenomas (for example villous colon adenoma), pathological angiogenesis and metastatic cell migration. The compounds are furthermore suitable for the treatment of complement activation dependent chronic inflammation (Niculescu et al. (2002) Immunol. Res., 24:191-199) and HIV-1 (human immunodeficiency virus type 1) induced immunodeficiency (Popik et al. (1998) J Virol, 72: 6406-6413).

Surprisingly, it has been found that compounds according to the invention are able to interact with signalling pathways, especially the signalling pathways described herein and preferably the Raf kinase signalling pathway. The compounds according to the invention preferably exhibit an advantageous biological activity which can easily be demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, these signalling pathways are relevant for various diseases. Accordingly, the compounds according to the invention are suitable for the prophylaxis and/or treatment of diseases that are dependent on the said signalling pathways by interacting with one or more of the said signalling pathways.

The present invention therefore relates to compounds according to the invention as promoters or inhibitors, preferably as inhibitors, of the signalling pathways described herein. The invention therefore preferably relates to compounds according to the invention as promoters or inhibitors, preferably as inhibitors, of the Raf kinase pathway. The invention therefore preferably relates to compounds according to the invention as promoters or inhibitors, preferably as inhibitors, of Raf kinase. The invention still more preferably relates to compounds according to the invention as promoters or inhibitors, preferably as inhibitors, of one or more Raf kinases selected from the group consisting of A-Raf, B-Raf and C-Raf-1. The invention particularly preferably relates to compounds according to the invention as promoters or inhibitors, preferably as inhibitors, of C-Raf-1.

The present invention furthermore relates to the use of one or more compounds according to the invention in the treatment and/or prophylaxis of diseases, preferably the diseases described herein, that are caused, mediated and/or propagated by Raf kinases and in particular diseases that are caused, mediated and/or propagated by Raf kinases selected from the group consisting of A-Raf, B-Raf and C-Raf-1. The diseases discussed here are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases. In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphomas, chronic leukaemia and acute leukaemia are to be regarded as cancerous diseases, all of which are usually regarded as hyperproliferative diseases. Especially cancerous cell growth and especially cancerous cell growth mediated by Raf kinase is a disease which is a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treat" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of kinase inhibitors, various assay systems are available. In the scintillation proximity assay (Sorg et al., J. of. Biomolecular Screening, 2002, 7, 11-19) and the flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

There are many diseases associated with deregulation of cell proliferation and cell death (apoptosis). The conditions of interest include, but are not limited to, the following. The compounds according to the invention are suitable for the treatment of a variety of conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, graft coronary vascular disease after transplantation, vein graft stenosis, peri-anastomotic prosthetic restenosis, restenosis after angioplasty or stent placement, and the like.

The compounds according to the invention are also suitable as p38 kinase inhibitors.

Other heteroarylureas which inhibit p38 kinase are described in WO 02/85859.

Prior Art

WO 02/44156 describes benzimidazole derivatives other than TIE-2 and/or VEGFR2 inhibitors. WO 99/32436 discloses substituted phenylureas as Raf kinase inhibitors. WO 02/062763 and WO 02/085857 disclose quinolyl-, isoquinolyl- and pyridylurea derivatives as Raf kinase inhibitors.

Heteroarylureas as p38 kinase inhibitors are described in WO 02/85859. ω-Carboxyaryldiphenylureas are described in WO 00/42012 as Raf kinase inhibitors and in WO 00/41698 as p38 kinase inhibitors. Other aryl- and heteroaryl-substituted heterocyclic ureas are disclosed in WO 99/32455 as Raf kinase inhibitors and in WO 99/32110 as p38 kinase inhibitors. Other diphenylurea derivatives are known from WO 99/32463. Substituted heterocyclic urea derivatives as p38 kinase inhibitors are disclosed in WO 99/32111.

SUMMARY OF THE INVENTION

The invention relates to compounds of the formula I

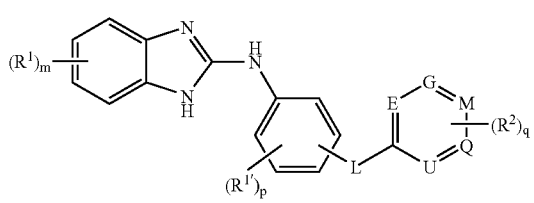

in which
R$^1$, R$^{1'}$ each, independently of one another, stand for Hal, A, OH, OA, SA, SO$_2$H, SO$_2$A, SO$_3$H, SO$_3$A, CN, NO$_2$, NH$_2$, NHA, NAA', NHCOA, CHO, C(=O)A, COOH, COOA, CONH$_2$, CONHA or CONAA',
L denotes CH$_2$, CH$_2$CH$_2$, O, S, SO, SO$_2$, NH, NA, C=O or CHOH,
R$^2$, independently, is selected from the meanings indicated for R$^1$ and R$^{1'}$ and is preferably, independently, selected from Hal, A, OH, OA, CN, COOH, COOA, CONH$_2$, CONHA or CONAA',
E, G, M,
Q and U each, independently of one another, stand for a C atom or an N atom,
A, A', independently of one another, are selected from unsubstituted or substituted alkyl having 1-10 C atoms, unsubstituted or substituted cycloalkyl having 3-10 C atoms, unsubstituted or substituted alkoxyalkyl having 2-12 C atoms, unsubstituted or substituted aryl having 6-14 C atoms, unsubstituted or substituted arylalkyl having 7-15 C atoms, unsubstituted or substituted, saturated, unsaturated or aromatic heterocyclyl having 2-7 C atoms and 1-3 hetero atoms selected from N, O and S, or unsubstituted or substituted, saturated, unsaturated or aromatic heterocyclylalkyl having 3-10 C atoms and 1-3 hetero atoms selected from N, O and S,
Hal denotes F, Cl, Br or I,
m, p, q each, independently of one another, denote 0, 1, 2, 3 or 4, and
n denotes 1, 2 or 3,
and pharmaceutically usable derivatives, solvates and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, such as, for example, $R^1$, their meanings are independent of one another.

Above and below, the radicals and parameters $R^1$, L, $R^{1'}$, $R^2$, m, p and q preferably have the meanings indicated for the formula I, unless expressly stated otherwise.

Above and below, the radicals A' are preferably, independently of one another, selected from the meanings indicated for the for the radicals A, unless expressly stated otherwise.

In the definition of A, alkyl is preferably unbranched (linear) or branched, has 1, 2, 3, 4, 5, 6, 7, 8, 9 or 10 C atoms and may be substituted. In the definition of A, substituted alkyl is an alkyl radical as described in this section, which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above. In the definition of A, substituted alkyl particularly preferably denotes an alkyl radical as described above in which 1-7H atoms have been replaced by F and/or chlorine, for example a perchlorinated or perfluorinated alkyl radical. Fluorine- and/or chlorine-substituted alkyl radicals of this type preferably have 1, 2, 3, 4 or 5 C atoms. Preferred fluorine- and/or chlorine-substituted alkyl radicals are perfluorinated alkyl radicals, in particular trifluoromethyl radicals. Unsubstituted or substituted alkyl particularly preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore particularly preferably trifluoromethyl. Alkyl very particularly preferably denotes an alkyl radical having 1, 2, 3, 4, 5 or 6 C atoms, which may be chlorinated and/or fluorinated as described above, and is, in particular, selected from methyl, ethyl, propyl, isopropyl, butyl, isobutyl, sec-butyl, tert-butyl, pentyl, hexyl, trifluoromethyl, pentafluoroethyl and 1,1,1-trifluoroethyl.

In the definition of A, unsubstituted cycloalkyl is preferably selected from cyclopropyl, cyclobutyl, cyclopentyl, cyclohexyl or cycloheptyl. In the definition of A, substituted cycloalkyl is a cycloalkyl radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above.

In the definition of A, unsubstituted alkoxyalkyl is a radical of the formula $C_uH_{2u+1}$—O—$(CH_2)_v$, in which u and v each, independently of one another, denote 1 to 6. The radical $C_uH_2u+_1$ preferably stands for an unbranched or branched alkyl radical as described above. Particularly preferably, u=1 or 2 and v=1, 2, 3 or 4. In the definition of A, substituted alkoxyalkyl is an alkoxyalkyl radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above.

For the purposes of this invention, alkylene is preferably an unbranched or branched divalent hydrocarbon radical having 1-10 C atoms, preferably 1-4 C atoms, which may optionally have 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above. Unsubstituted alkylene preferably stands for methylene, ethylene, n-propylene, isopropylene or n-butylene and in particular for methylene or ethylene.

In the definition of A, unsubstituted aryl is preferably a benzene ring, for example a phenyl radical, or a system of benzene rings, such as, for example, anthracene, phenanthrene or naphthalene ring systems or radicals. In the definition of A, substituted aryl is an aryl radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above.

In the definition of A, unsubstituted arylalkyl is an aryl radical as defined above connected to an alkylene radical as defined above. Examples of preferred unsubstituted arylalkyl radicals are benzyl, phenethyl, phenylpropyl and phenylbutyl and in particular benzyl and phenethyl. In the definition of A, substituted arylalkyl is an arylalkyl radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above.

In the definition of A, unsubstituted saturated, unsaturated or aromatic heterocyclyl is a heterocyclic radical having 2-7 C atoms and 1-3 hetero atoms selected from N, O and S. Examples of preferred unsubstituted saturated heterocyclyl are 1-piperidyl, 1-piperazyl, 4-morpholinyl, 1-pyrrolidinyl, 1-pyrazolidinyl, 1-imidazolidinyl, tetrahydrofuran-2-yl and tetrahydrofuran-3-yl. Examples of unsubstituted, unsaturated or aromatic heterocyclyl are thiophen-2-yl and thiophen-3-yl, furan-2-yl and furan-3-yl, pyrrol-2-yl and pyrrol-3-yl, 2-, 3- and 4-pyridyl, 2-, 4- and 5-oxazolyl, 2-, 4- and 5-thiazolyl, quinolinyl, isoquinolinyl, 2- and 4-pyridazyl, 2-, 4- and 5-pyrimidyl, and 2- and 3-pyrazinyl. In the definition of A, substituted saturated, unsaturated or aromatic heterocyclyl is a heterocyclic radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above. Examples of substituted, saturated, unsaturated or aromatic heterocyclyl and in particular substituted saturated heterocyclyl are 1-(4-methyl)piperazyl, 4-methylpiperazin-1-ylamine, 1-(2-methyl)pyrazolidinyl and 1-(3-methyl)imidazolidinyl.

In the definition of A, unsubstituted heterocyclylalkyl is a heterocyclyl radical as defined above connected to an alkylene radical as defined above. In the definition of A, substituted heterocyclylalkyl is a heterocyclylalkyl radical as described above which has 1-7, preferably 1-5 and particularly preferably 1-3 substituents, which are preferably selected from Hal, in particular Cl and F, OH, Oalkyl, $NH_2$ and $N(alkyl)_2$, in which alkyl is as described above and is preferably unsubstituted alkyl as described above.

The comments and meanings indicated in the previous paragraphs in the definition of A preferably apply correspondingly in the definition of A' too.

$R^1$ is preferably selected from A, where A is as defined above and here preferably stands for unsubstituted and/or substituted alkyl and in particular for methyl, ethyl, propyl, isopropyl, butyl, isobutyl, sec-butyl, tert-butyl, pentyl, hexyl, trifluoromethyl, pentafluoroethyl, and/or 1,1,1-trifluoroethyl, COOH, COOA; in which A is as defined above and preferably stands for unsubstituted or substituted, particularly preferably unsubstituted alkyl and in particular for methyl or ethyl, $SO_2A$, in which A is as defined above and preferably stands for unsubstituted or substituted, particularly preferably unsubstituted alkyl and in particular for trifluoromethyl, methyl or ethyl, CN, $NO_2$, Hal, in particular F, Cl and/or Br, and C(=O)A, in which A is as defined above and preferably stands for unsubstituted or substituted alkyl, unsubstituted or substituted, preferably unsubstituted, saturated, unsaturated or aromatic, preferably unsaturated or aromatic, heterocyclyl and in particular for thiophen-2-yl or thiophen-3-yl.

$R^1$ is particularly preferably selected from F, Cl, Br, methyl, ethyl, propyl, isopropyl, butyl, isobutyl, sec-butyl, tert-butyl, trifluoromethyl, pentafluoroethyl, 1,1,1-trifluoroethyl, CN, $NO_2$, COOH, $COOCH_3$, $COOCH_2CH_3$, $SO_2CH_3$, $SO_2CF_3$ and C(=O)A, in which A stands for thiophen-2-yl.

$R^1$ is particularly preferably selected from methyl, trifluoromethyl, F, Cl, Br, CN, $NO_2$, COOH, $COOCH_3$, $SO_2CH_3$ and C(=O)A, in which A stands for thiophen-2-yl.

In a preferred embodiment, $R^1$ is selected from methyl, trifluoromethyl, F, Cl and Br.

In a further preferred embodiment, $R^1$ is selected from CN, $NO_2$, COOH, $COOCH_3$, $SO_2CH_3$ and C(=O)A, in which A stands for thiophen-2-yl.

$R^{1'}$ is preferably selected from A, where A is as defined above and here preferably stands for unsubstituted and/or substituted alkyl and in particular for methyl, ethyl, propyl, isopropyl, butyl, isobutyl, sec-butyl, tert-butyl, pentyl, hexyl, trifluoromethyl, pentafluoroethyl, and/or 1,1,1-trifluoroethyl, COOH, COOA, in which A is as defined above and preferably stands for unsubstituted or substituted, particularly preferably unsubstituted alkyl and in particular for methyl or ethyl, CN, $NO_2$, Hal, in particular F, Cl and/or Br.

$R^{1'}$ is particularly preferably selected from unsubstituted or substituted alkyl, in particular methyl, ethyl, propyl, isopropyl, butyl, isobutyl, sec-butyl, tert-butyl, pentyl, hexyl, trifluoromethyl, pentafluoroethyl, 1,1,1-trifluoroethyl, and halogen, in particular F, Cl and/or Br. $R^1$ is very particularly preferably selected from methyl, ethyl, propyl, fluorine and bromine.

L preferably denotes O, S or $CH_2$, particularly preferably O.

$R^2$ is preferably selected from A, where A is as defined above and here preferably stands for unsubstituted and/or substituted alkyl and in particular for methyl, ethyl, propyl, isopropyl, butyl, isobutyl, sec-butyl, tert-butyl, pentyl, hexyl, trifluoromethyl, pentafluoroethyl, and/or 1,1,1-trifluoroethyl, Hal, in particular F, Cl and/or Br, CN, $NO_2$, COOH, $CONH_2$, $NH_2$, and NHA, NAA', COOA, CONHA and CONAA', in which A and A' are as defined above and preferably stand for unsubstituted or substituted, particularly preferably unsubstituted alkyl and in particular for methyl propyl, isopropyl, butyl, isobutyl, sec-butyl, tert-butyl or ethyl.

$R^2$ is particularly preferably selected from F, Cl, Br, methyl, ethyl, propyl, isopropyl, butyl, isobutyl, sec-butyl, tert-butyl, trifluoromethyl, pentafluoroethyl, 1,1,1-trifluoroethyl, CN, $NO_2$, $NH_2$, $NHCH_3$, $N(CH_3)_2$, COOH, $COOCH_3$, $COOCH_2CH_3$, $CONH_2$, $CONHCH_3$, $CONHCH_2CH_3$, $CON(CH_3)_2$, $SO_2CH_3$, and $SO_2CF_3$.

$R^2$ is very particularly preferably selected from methyl, ethyl, methoxycarbonyl, ethoxycarbonyl, $NH_2$, $CONH_2$, $CONHCH_3$, $CONHCH_2CH_3$ and $CON(CH_3)_2$.

E, G, M, Q and U each, independently of one another, stand for a C atom or an N atom, where at least one thereof, E, G, M, Q or U, preferably stands for N. One, two or three, particularly preferably one or two, of E, G, M, Q and U preferably stand for an N atom. If one selected from E, G, M, Q and U stands for an N atom, M, G or Q preferably stands for an N atom. If two selected from E, G, M, Q and U stand for N atoms, E and M or U and Q preferably stand for N atoms.

The substituents $R^2$ preferably bond to carbon atoms. If one or more of E, G, M, Q and U stand for C atoms, each C atom is therefore preferably selected from CH or $CR^2$, where $R^2$ is selected independently on each $CR^2$.

The E-, G-, M-, Q- and U-containing aromatic or preferably heteroaromatic radical bonded to L is therefore preferably selected from phenyl, pyridyl, pyrimidyl, pyridazinyl, pyrazinyl, triazinyl, preferably 1,2,4-triazinyl and 1,3,5-triazinyl, particularly preferably from pyridyl, pyrimidyl, pyridazinyl and pyrazinyl and in particular from pyridyl and pyrimidyl, which optionally has 1, 2 or 3, preferably no, one or two substituents $R^2$ selected independently of one another, which are preferably bonded to a C atom of the abovementioned aromatic or heteroaromatic radicals.

m or p or q is preferably different from 0. Particularly preferably, m is different from 0 and in addition p or q is different from 0. Particularly preferably, m is different from 0 and in addition p or q is different from 0.

m preferably denotes 1, 2 or 3 and particularly preferably 2 or 3. p preferably denotes 0 or 1 and particularly preferably 0. q preferably denotes 0, 1 or 2 and particularly preferably 0 or 1, or likewise preferably 1 or 2.

Preference is furthermore given to compounds as described above/below in which $R^2$ denotes A, COOA, CONA or $CONH_2$, and q denotes 0, 1 or 2, and pharmaceutically usable derivatives, solvates and stereoisomers thereof, including mixtures thereof in all ratios.

In the compounds of the formula I, the group

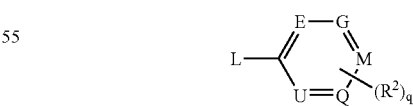

is preferably selected from

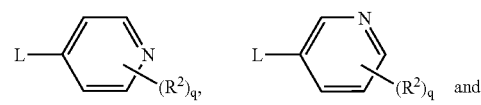

-continued

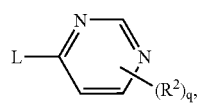

in which L, $R^2$ and q have the meanings indicated above/below. q here is preferably selected from 0 and 1, or likewise preferably selected from 1 and 2.

In the compounds of the formula I, the group

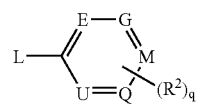

is particularly preferably selected from

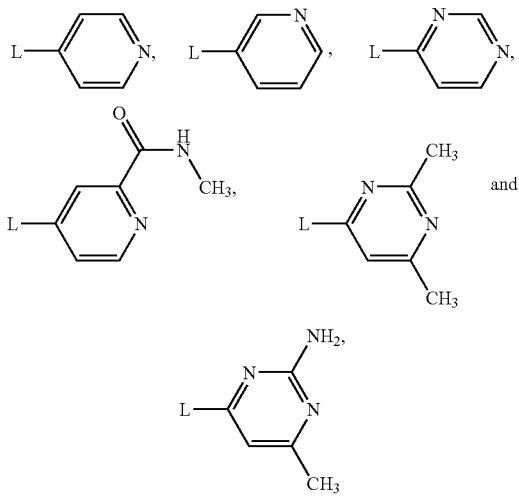

in which L has the meaning indicated above/below, and in particular selected from

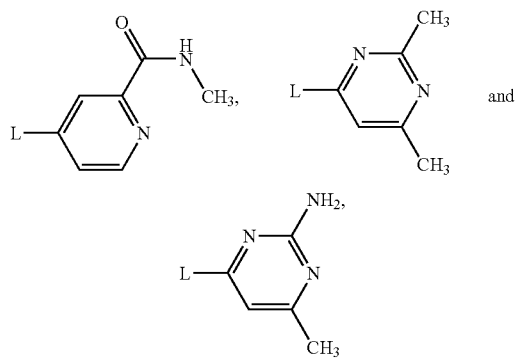

in which L has the meaning indicated above/below.

In the compounds of the formula I, the group

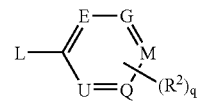

is preferably not fused, i.e. the six-membered aromatic, E-, G-, M-, Q- and U-containing ring is preferably not fused, but instead preferably represents a monocyclic aromatic and in particular a monocyclic heteroaromatic ring, since the radical $R^2$ or the radicals $R^2$ preferably do not stand for fused-on or fusing radicals.

Particularly preferred compounds of the formula I are compounds of the formula Ia

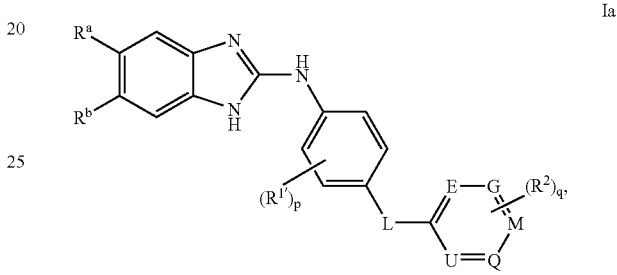

Ia in which $R^a$ and $R^b$ are selected, independently of one another, from the meanings indicated for $R^1$ and particularly preferably from the meanings indicated as preferred, particularly preferred or especially preferred for $R^1$. It is particularly preferred in the compounds of the formula Ia for one of the two radicals $R^a$ or $R^b$ to be other than H or for both radicals $R^a$ and $R^b$ to be other than H. Particular preference is given to compounds of the formula Ia in which $R^a$=Cl and $R^b$=CF$_3$; $R^a$=H and $R^b$=CF$_3$; $R^a$=H and $R^b$=CH$_3$; $R^a$=CH$_3$ and $R^b$=CH$_3$; $R^a$=Cl and $R^b$=Cl; $R^a$=Cl and $R^b$=H; $R^a$=Cl and $R^b$=CH$_3$; $R^a$=H and $R^b$=NO$_2$; $R^a$=H and $R^b$=CN; $R^a$=H and $R^b$=COOH; $R^a$=H and $R^b$=COOCH$_3$; $R^a$=H and $R^b$=thiophen-2-yl-carbonyl; and/or $R^a$=H and $R^b$=NH$_2$.

Particularly preferred compounds of the formula I are compounds of the formula Ib

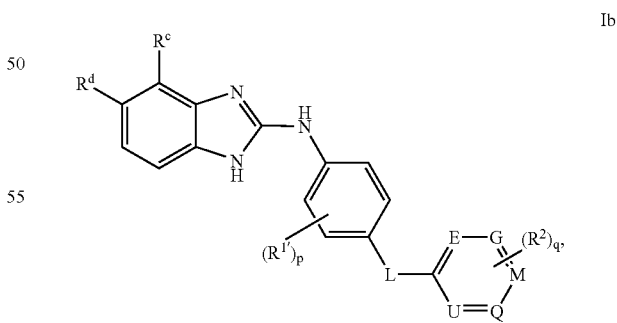

Ib in which $R^c$ and $R^d$ are selected, independently of one another, from the meanings indicated for $R^1$ and particularly preferably from the meanings indicated as preferred, particularly preferred or especially preferred for $R^1$.

It is particularly preferred It is particularly preferred in the compounds of the formula Ib for one of the two radicals $R^c$ or R$^d$ to be other than H or for both radicals R$^c$ and R$^d$ to be other than H. Particular preference is given to compounds of the formula Ib in which R$^c$=CH$_3$ and R$^d$=Cl; R$^c$=CH$_3$ and R$^d$=H; and/or R$^c$=CH$_3$ and R$^d$=CH$_3$.

Particularly preferred compounds of the formula I are compounds of the formula Ic

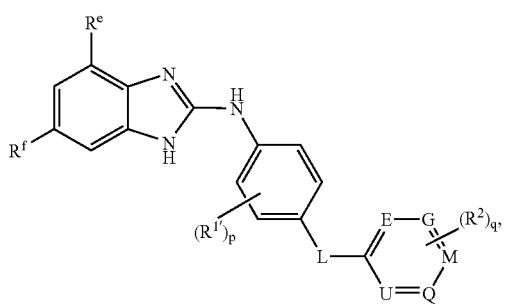

Ic in which R$^e$ and R$^f$ are selected, independently of one another, from H and the meanings indicated for R$^1$ and particularly preferably from H and the meanings indicated as preferred, particularly preferred or especially preferred for R$^1$. It is particularly preferred It is particularly preferred in the compounds of the formula Ic for one of the two radicals R$^e$ or R$^f$ to be other than H or for both radicals R$^e$ and R$^f$ to be other than H. Particular preference is given to compounds of the formula Ic in which R$^e$=Br and R$^f$=CF$_3$; R$^e$=Cl and R$^f$=CF$_3$; R$^e$=CF$_3$ and R$^f$=CF$_3$; R$^e$=F and R$^f$=CF$_3$; R$^e$=SO$_2$CH$_3$ and R$^f$=Cl; R$^e$=SO$_2$CH$_3$ and R$^f$=COOCH$_3$; R$^e$=CH$_3$ and R$^f$=Cl; R$^e$=Cl and R$_f$=H; R$^e$Cl and R$^f$=CH$_3$; R$^e$=H and R$_f$=NO$_2$; R$^e$=H and R$^e$CN; R$^e$=H and R$^f$=COOH; R$^e$=H and R$^f$=COOCH$_3$; R$^e$=H and R$_f$=thiophen-2-ylcarbonyl; or R$^e$=H and R$_f$=NH$_2$. Very particular preference is given to compounds of the formula Ic in which R$^e$=Br and R$^f$=CF$_3$; R$^e$=Cl and R$^f$=CF$_3$; R$^e$=CF$_3$ and R$^f$=CF$_3$; R$^e$=F and R$^f$=CF$_3$; R$^e$=SO$_2$CH$_3$ and R$^f$=Cl; R$^e$=Cl and R$_f$=H; R$^e$=Cl and R$^f$=CH$_3$; R$^e$=H and R$^e$=NO$_2$; R$^e$=H and R$^f$=CN; R$^e$=H and R$^f$=COOH; R$^e$=H and R$^f$=COOCH$_3$; R$^e$=H and R$^f$ thiophen-2-ylcarbonyl; or R$^e$=H and R$^f$=NH$_2$. Very particular preference is likewise given to compounds of the formula Ic in which R$^e$=SO$_2$CH$_3$ and R$^f$=COOCH$_3$ and/or R$^e$=CH$_3$ and R$^f$=Cl.

In the compounds of the formulae Ia, Ib and/or Ic, R$^{1'}$, p L, E, G, M, Q, U, R$^2$ and q have the meanings indicated above/below.

A reference to the compounds of the formula I includes the reference to all associated sub-formulae and/or part-formulae, in particular sub-formulae Ia, Ib and/or Ic and preferably part-formulae I.1) to I.12), unless indicated otherwise.

The compounds of the formula I can have one or more centres of chirality and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following part-formulae I.1) to I.12), which conform to the formula I and in which the radicals not designated in greater detail have the meaning indicated for the formula I, but in which in I.1) R$^1$, independently of one another, denotes A or Hal, preferably alkyl or Hal, and
m denotes 1, 2 or 3;

in I.2) R$^1$, independently of one another, denotes CH$_3$, CF$_3$, F or Br, and
m denotes 1, 2 or 3;

in I.3) R$^1$, independently of one another, denotes CN, COOH, COOA, SO$_2$A, SO$_3$A, C(=O)A, NH$_2$, NHA or NO$_2$, and
m denotes 1, 2 or 3, preferably 1 or 2;

in I.4) R$^1$, independently of one another, denotes CN, COOH, COOalkyl, SO$_2$alkyl, SO$_3$alkyl, NH$_2$, NHalkyl, C(=O)alkyl, C(=O)heterocyclyl or NO$_2$, and
m denotes 1, 2 or 3, preferably 1 or 2;

in I.5) R$^1$, independently of one another, denotes Hal, alkyl, CN, COOH, COOalkyl, SO$_2$alkyl, SO$_3$alkyl, NH$_2$, NHalkyl, C(=O)alkyl, C(=O)heterocyclyl or NO$_2$,
m denotes 1, 2 or 3, preferably 1 or 2
R$^{1'}$ denotes Hal or A, preferably Hal or alkyl, and
p denotes 0 or 1;

in I.6) R$^1$, independently of one another, denotes Hal, alkyl, CN, COOH, COOalkyl, SO$_2$alkyl, SO$_3$alkyl, NH$_2$, NHalkyl, C(=O)alkyl, C(=O)heterocyclyl or NO$_2$,
m denotes 1, 2 or 3, preferably 1 or 2,
R$^1$ denotes Hal or A, preferably Hal or alkyl,
p denotes 0 or 1, and
L denotes O, S or CH$_2$, preferably O or CH$_2$;

in I.7) R$^1$, independently of one another, denotes Hal, alkyl, CN, COOH, COalkyl, SO$_2$alkyl, SO$_3$alkyl, NH$_2$, NHalkyl, C(=O)alkyl, C(=O)heterocyclyl or NO$_2$,
m denotes 1, 2 or 3, preferably 1 or 2,
R$^{1'}$ denotes Hal or A, preferably Hal or alkyl,
p denotes 0 or 1, and
L denotes O, S or CH$_2$, preferably O or CH$_2$;

in I.8) R$^1$, independently of one another, denotes Hal, alkyl, CN, COOH, COalkyl, SO$_2$alkyl, SO$_3$alkyl, NH$_2$, NHalkyl, C(=O)alkyl, C(=O)heterocyclyl or NO$_2$,
m denotes 1, 2 or 3, preferably 1 or 2,
R$^{1'}$ denotes Hal or A, preferably Hal or alkyl,
p denotes 0 or 1,
L denotes O, S or CH$_2$, preferably O or CH$_2$,
R$^2$ denotes A, COOA, CONHA or CONH$_2$, preferably COOalkyl, CONHalkyl or CONH$_2$, and
q denotes 0, 1 or 2;

in I.9) R$^1$, independently of one another, denotes Hal, alkyl, CN, COOH, COOalkyl, SO$_2$alkyl, SO$_3$alkyl, NH$_2$, NHalkyl, C(=O)alkyl, C(=O)heterocyclyl or NO$_2$,
m denotes 1, 2 or 3, preferably 1 or 2,
R$^{1'}$ denotes Hal or A, preferably Hal or alkyl,
p denotes 0 or 1,
L denotes O, S or CH$_2$, preferably O or CH$_2$,
R$^2$ denotes A, COOA, CONHA or CONH$_2$, preferably COalkyl, CONHalkyl or CONH$_2$,
q denotes 0, 1 or 2,
and the group

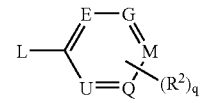

is selected from

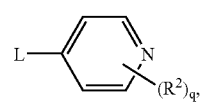 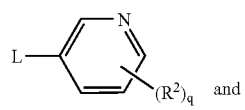 and

-continued

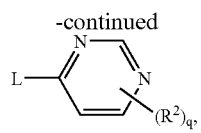

in which L, R² and q have the meanings indicated above;
in I.10) R¹' denotes Hal or A, preferably Hal or alkyl,
p denotes 0 or 1,
L denotes O, S or CH₂, preferably O or CH₂,
R² denotes A, COOA, CONHA or CONH₂, preferably COalkyl, CONHalkyl or CONH₂,
q denotes 0, 1 or 2,
and the group

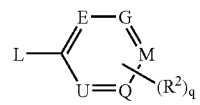

has the meaning indicated in 1.9);
in I.11) L denotes O, S or CH₂, preferably O or CH₂,
R² denotes A, COOA, CONHA or CONH₂, preferably COOalkyl, CONHalkyl or CONH₂,
q denotes 0, 1 or 2,
and the group

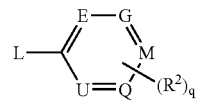

has the meaning indicated in 1.9);
in I.12) R² denotes A, COOA, CONHA or CONH₂, preferably COOalkyl, CONHalkyl or CONH₂,
q denotes 0, 1 or 2,
and the group

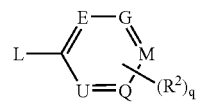

has the meaning indicated in 1.9);
and pharmaceutically usable derivatives, solvates and stereoisomers thereof, including mixtures thereof in all ratios.

Particular preference is given to the compounds according to the invention selected from compounds (1) to (41):

(1)

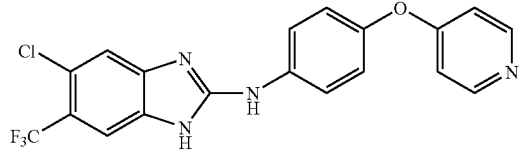

(5-Chloro-6-trifluoromethyl-1H-benzimidazol-2-yl)[4-(pyridin-4-yloxy)-phenyl]amine (2)

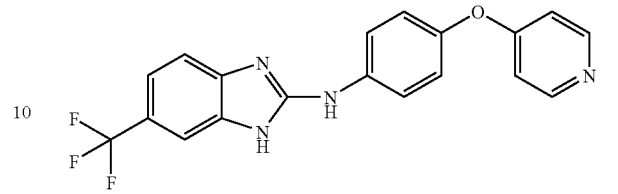

[4-(Pyridin-4-yloxy)phenyl](6-trifluoromethyl-1H-benzimidazol-2-yl)amine (3)

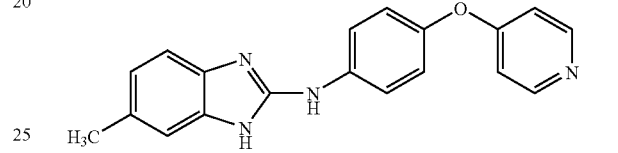

(6-Methyl-1H-benzimidazol-2-yl)[4-(pyridin-4-yloxy)phenyl]amine (4)

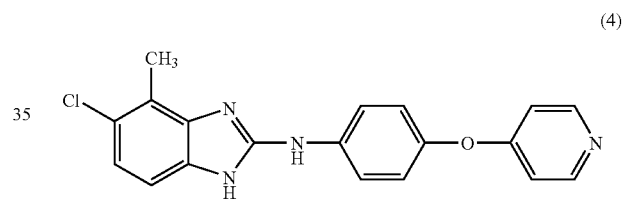

(5-Chloro-4-methyl-1H-benzimidazol-2-yl)[4-(pyridin-4-yloxy)phenyl]-amine (5)

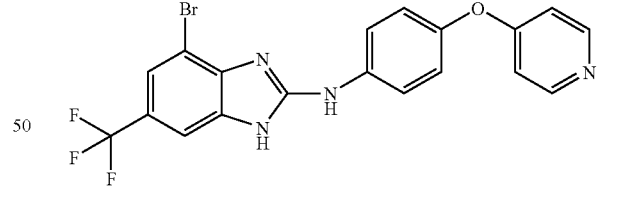

(4-Bromo-6-trifluoromethyl-1H-benzimidazol-2-yl)[4-(pyridin-4-yloxy)phenyl]amine (6)

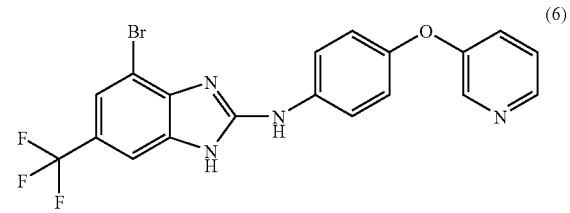

(4-Bromo-6-trifluoromethyl-1H-benzimidazol-2-yl)[4-(pyridin-3-yloxy)phenyl]amine (5-Chloro-1H-benzimidazol-2-yl)[4-(pyridin-4-yloxy)phenyl]amine

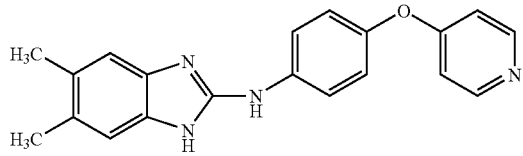
(7)

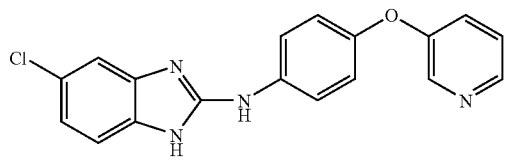
(12)

(5,6-Dimethyl-1H-benzimidazol-2-yl)[4-(pyridin-4-yloxy)phenyl]amine (5-Chloro-1H-benzimidazol-2-yl)[4-(pyridin-3-yloxy)phenyl]amine

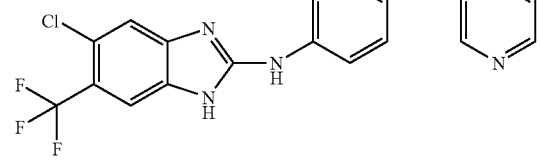
(8)

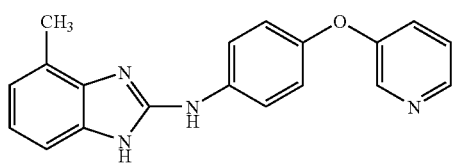
(13)

(5-Chloro-6-trifluoromethyl-1H-benzimidazol-2-yl)[4-(pyridin-3-yloxy)phenyl]amine (4-Methyl-1H-benzimidazol-2-yl)[4-(pyridin-3-yloxy)phenyl]amine

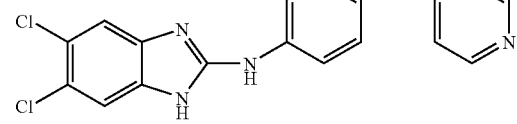
(9)

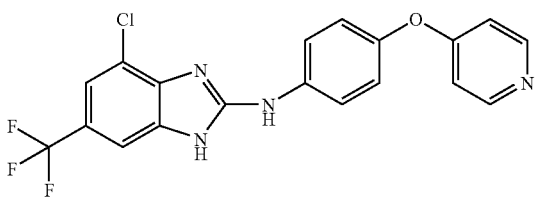
(14)

(5,6-Dichloro-1H-benzimidazol-2-yl)[4-(pyridin-4-yloxy)phenyl]amine (4-Chloro-6-trifluoromethyl-1H-benzimidazol-2-yl)[4-(pyridin-4-yloxy)phenyl]amine

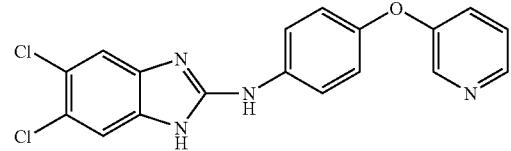
(10)

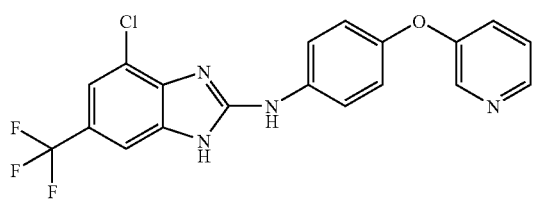
(15)

(5,6-Dichloro-1H-benzimidazol-2-yl)[4-(pyridin-3-yloxy)phenyl]amine (4-Chloro-6-trifluoromethyl-1H-benzimidazol-2-yl)[4-(pyridin-3-yloxy)phenyl]amine

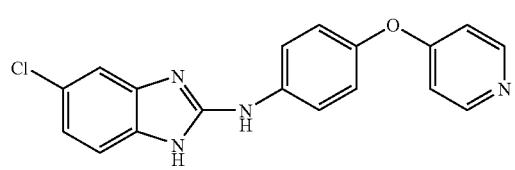
(11)

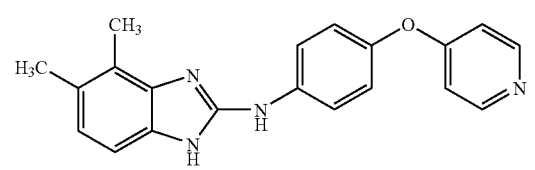
(16)

(4,5-Dimethyl-1H-benzimidazol-2-yl)[4-(pyridin-4-yloxy)phenyl]amine

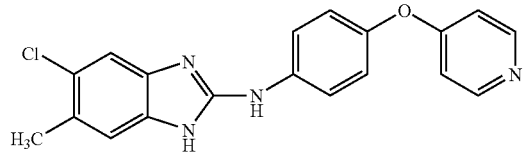

(5-Chloro-6-methyl-1H-benzimidazol-2-yl)[4-(pyridin-4-yloxy)phenyl]-amine (17)

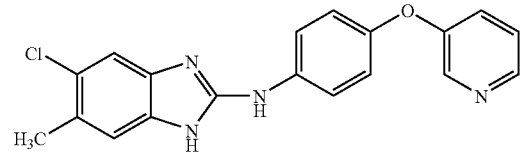

(5-Chloro-6-methyl-1H-benzimidazol-2-yl)[4-(pyridin-3-yloxy)phenyl]-amine (18)

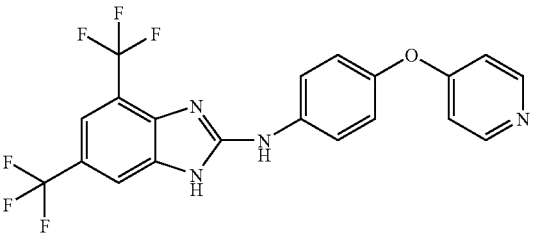

(4,6-Bistrifluoromethyl-1H-benzimidazol-2-yl)[4-(pyridin-4-yloxy)phenyl]amine (19)

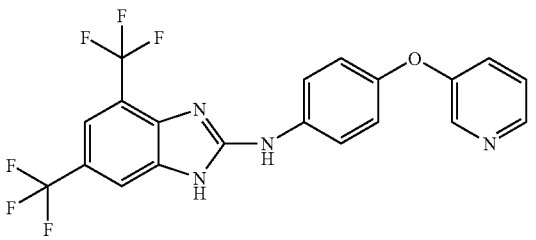

(20)

(4,6-Bistrifluoromethyl-1H-benzimidazol-2-yl)[4-(pyridin-3-yloxy)phenyl]amine

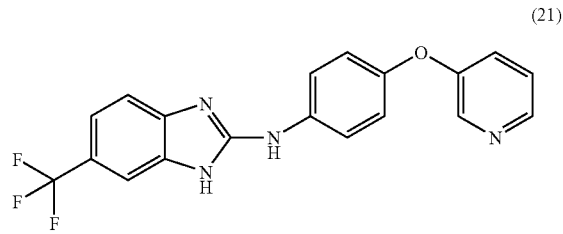

[4-(Pyridin-3-yloxy)phenyl](6-trifluoromethyl-1H-benzimidazol-2-yl)amine (21)

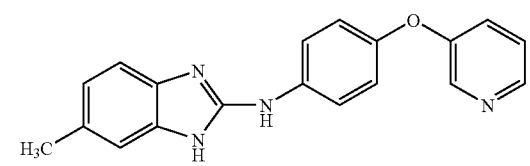

(6-Methyl-1H-benzimidazol-2-yl)[4-(pyridin-3-yloxy)phenyl]amine (22)

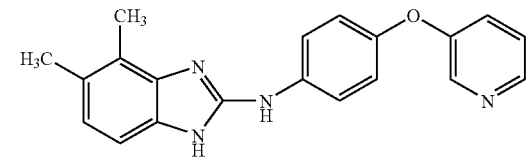

(4,5-Dimethyl-1H-benzimidazol-2-yl)[4-(pyridin-3-yloxy)phenyl]amine (23)

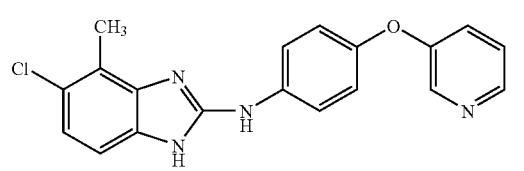

(5-Chloro-4-methyl-1H-benzimidazol-2-yl)[4-(pyridin-3-yloxy)phenyl]-amine (24)

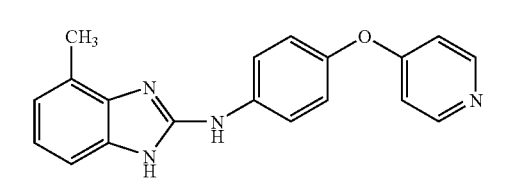

(25)

(4-Methyl-1H-benzimidazol-2-yl)[4-(pyridin-4-yloxy)phenyl]amine

2-[4-(Pyridin-4-yloxy)phenylamino]-3H-benzimidazole-5-carbonitrile

(26)
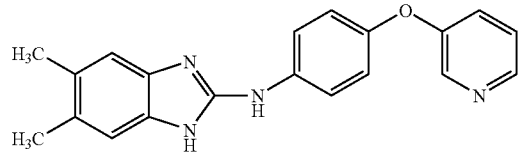
(5,6-Dimethyl-1H-benzimidazol-2-yl)[4-(pyridin-3-yloxy)phenyl]amine

(30)
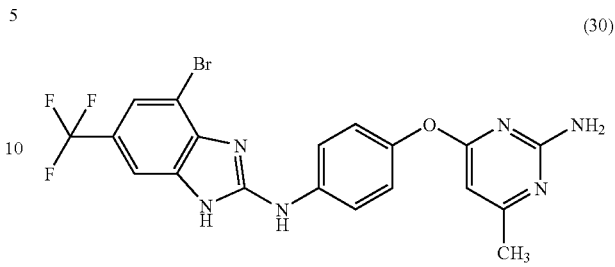
[4-(2-Amino-6-methylpyrimidin-4-yloxy)phenyl](4-bromo-6-trifluoromethyl-1H-benzimidazol-2-yl)amine

(27)
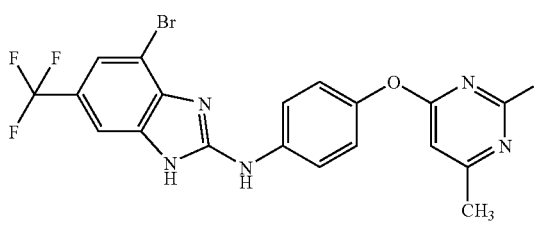
(4-Bromo-6-trifluoromethyl-1H-benzimidazol-2-yl)[4-(2,6-dimethylpyrimidin-4-yloxy)phenyl]amine

(31)
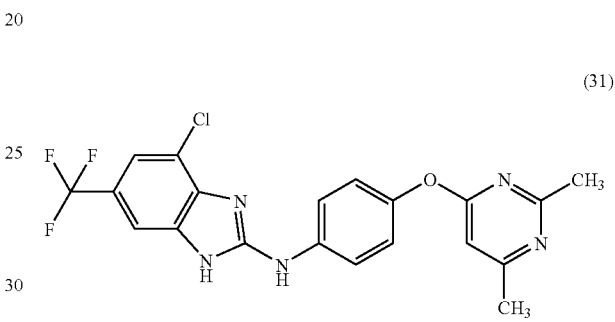
(4-Chloro-6-trifluoromethyl-1H-benzimidazol-2-yl)[4-(2,6-dimethylpyrimidin-4-yloxy)phenyl]amine

(28)
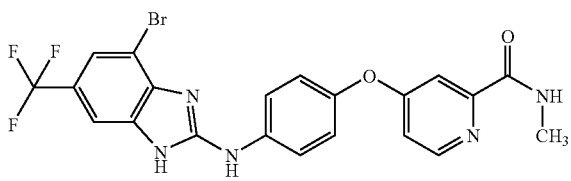
N-Methyl-4-[4-(bromotrifluoromethyl-1H-benzimidazol-2-ylamino)phenoxy]pyridine-2-carboxamide

(32)
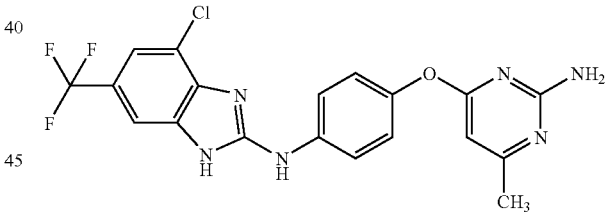
[4-(2-Amino-6-methylpyrimidin-4-yloxy)phenyl](4-chloro-6-trifluoromethyl-1H-benzimidazol-2-yl)amine

(29)
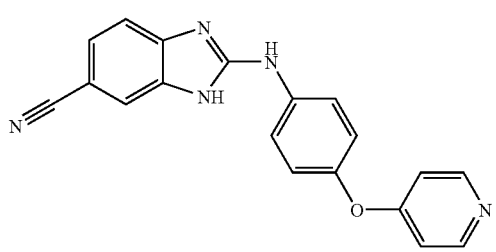

(33)
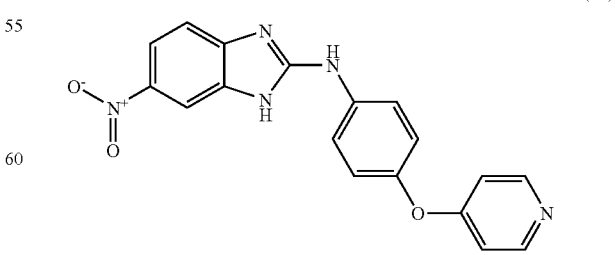

(6-Nitro-1H-benzimidazol-2-yl)[4-(pyridin-4-yloxy)phenyl]amine

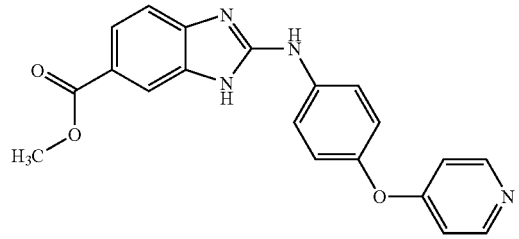

Methyl 2-[4-(pyridin-4-yloxy)phenylamino]-3H-benzimidazole-5-carboxylate

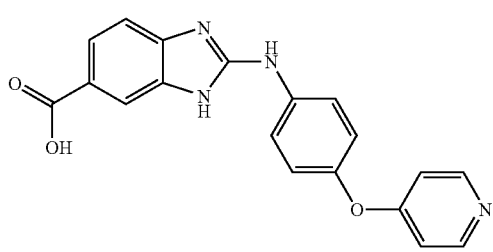

2-[4-(Pyridin-4-yloxy)phenylamino]-3H-benzimidazole-5-carboxylic acid

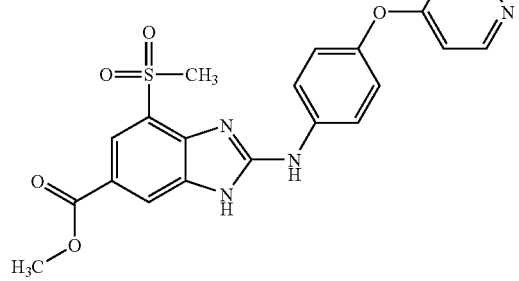

Methyl 7-methanesulfonyl-2-[4-(pyridin-4-yloxy)phenylamino]-3H-benzimidazole-5-carboxylate

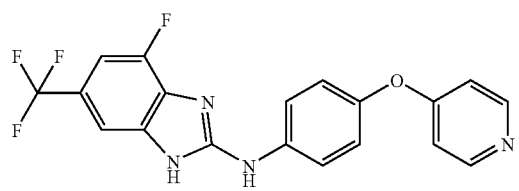

(4-Fluoro-6-trifluoromethyl-1H-benzimidazol-2-yl)[4-(pyridin-4-yloxy)phenyl]amine

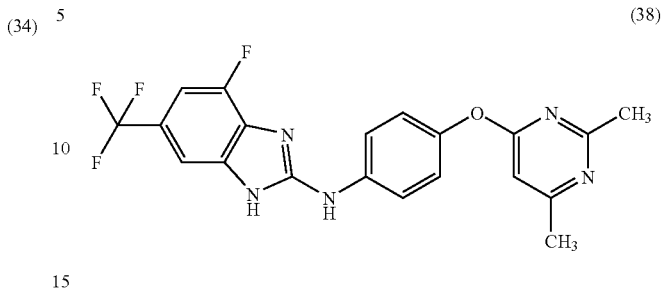

[4-(2,6-Dimethylpyrimidin-4-yloxy)phenyl](4-fluoro-6-trifluoromethyl-1H-benzimidazol-2-yl)amine

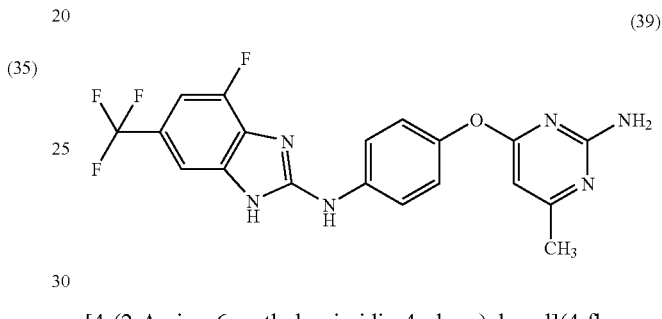

[4-(2-Amino-6-methylpyrimidin-4-yloxy)phenyl](4-fluoro-6-trifluoromethyl-1H-benzimidazol-2-yl)amine

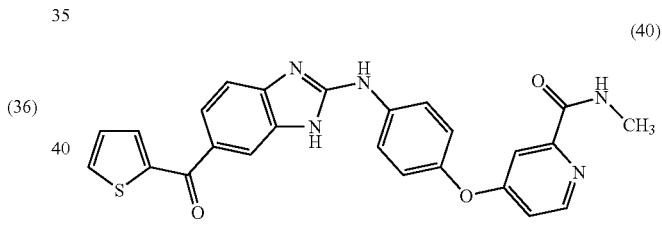

N-Methyl-4-{4-[6-(1-thiophen-2-ylmethanoyl)-1H-benzimidazol-2-ylamino]phenoxy}pyridine-2-carboxamide $N^2$-[4-(Pyridin-4-yloxy)phenyl]-3H-benzimidazole-2,5-diamine The invention relates to the compounds of the formula I and salts thereof and to a process for the preparation of compounds of the formula I as described above/below and pharmaceutically usable derivatives, solvates and stereoisomers thereof, characterised in that a compound of the formula II

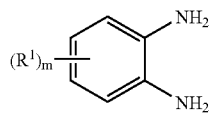

in which $R^1$ and m have the meanings indicated above/below, is reacted with a compound of the formula III

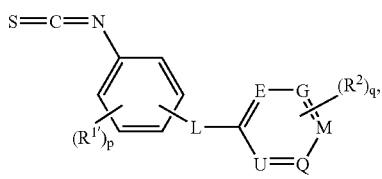

in which $R^{1'}$, L, E, G, M, Q, U, $R^2$ and q have the meanings indicated above/below, if desired, the resultant compound of the formula I is isolated, and/or a base or acid of the formula I is converted into one of its salts.

The compounds according to the invention and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds according to the invention.

Compounds of the formula I are preferably obtained by reacting compounds of the formulae II with compounds of the formula III.

The reaction is generally carried out in an inert solvent, in the presence of a coupling reagent, such as, for example, N,N'-diisopropylcarbodiimide. Depending on the conditions used, the reaction time is between a few minutes and 14 days, the reaction temperature is between about 0° and 200°, normally between 20° and 150° and in particular between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds are generally known. If they are novel, however, they can be prepared by methods known per se. The thioisocyanates of the formula III are preferably [lacuna] from the corresponding aniline derivatives by reaction with, for example, 1,1'-thiocarbonyldiimidazole.

A base of the compounds according to the invention can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds according to the invention.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting maquine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas. Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound according to the invention and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds according to the invention and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small cell lung carcinomas, pancreatic cancer, glioblastomas and breast carcinoma.

Also encompassed is the use of the compounds according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds according to the invention and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds according to the invention and/or physiologically acceptable salts and solvates thereof for the preparation of a medicament for the treatment or prevention of a tyrosine kinase-induced disease or a tyrosine kinase-induced condition in a mammal, in which a therapeutically effective amount of a compound according to the invention is administered to this method to a sick mammal in need of such treatment. The therapeutic amount varies according to the specific disease and can be determined by the person skilled in the art without undue effort.

The present invention also encompasses the use of the compounds according to the invention and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds according to the invention can be administered to patients for the treatment of cancer. The present compounds inhibit tumour angiogenesis, thereby affecting the growth of tumours (J. Rak et al. *Cancer Research*, 55:4575-4580,1995). The angiogenesis-inhibiting properties of the compounds according to the invention are also suitable for the treatment of certain forms of blindness related to retinal neovascularisation. The compounds according to the invention are also suitable for the treatment of certain bone pathologies, such as osteosarcoma, osteoarthritis and rickets, also known as oncogenic osteomalacia (Hasegawa et al., Skeletal Radiol. 28, pp. 41-45,1999; Gerber et al., Nature Medicine, Vol. 5, No. 6, pp. 623-628, June 1999). Since VEGF directly promotes osteoclastic bone resorption through KDR/FIk-1 expressed in mature osteoclasts (FEBS Let. 473:161-164 (2000); Endocrinology, 141:1667 (2000)), the present compounds are also suitable for the treatment and prevention of conditions related to bone resorption, such as osteoporosis and Paget's disease.

The compounds can also be used for the reduction or prevention of tissue damage which occurs after cerebral ischaemic events, such as strokes, by reducing cerebral oedema, tissue damage and reperfusion injury following ischaemia (*Drug News Perspect* 11:265-270 (1998); *J. Clin. Invest.* 104:1613-1620 (1999)).

The invention thus relates to the use of compounds according to the invention and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to kinases selected from the group of the tyrosine kinases and Raf kinases.

The tyrosine kinases are preferably TIE-2.

Preference is given to the use of compounds according to claim 1, and pharmaceutically usable derivatives, solvates and stereoisomers thereof, including mixtures thereof in all ratios, for the preparation of a medicament for the treatment of diseases which are influenced by inhibition of tyrosine kinases by the compounds according to the invention.

Particular preference is given to the use for the preparation of a medicament for the treatment of diseases which are influenced by inhibition of TIE-2 by the compounds according to the invention.

Especial preference is given to the use for the treatment of a disease, where the disease is a solid tumour.

The solid tumour is preferably selected from the group of brain tumour, tumour of the urogenital tract, tumour of the lymphatic system, stomach tumour, laryngeal tumour and lung tumour.

The solid tumour is furthermore preferably selected from the group of monocytic leukaemia, lung adenocarcinoma, small cell lung carcinomas, pancreatic cancer, glioblastomas and breast carcinoma.

The invention furthermore relates to the use of the compounds according to the invention for the treatment of a disease in which angiogenesis is implicated.

The disease is preferably an ocular disease.

The invention furthermore relates to the use for the treatment of retinal vascularisation, diabetic retinopathy, age-induced macular degeneration and/or inflammatory diseases.

The inflammatory disease is preferably selected from the group of rheumatoid arthritis, psoriasis, contact dermatitis and delayed hypersensitivity reaction.

The invention furthermore relates to the use of the compounds according to the invention for the treatment of bone pathologies, where the bone pathology originates from the group osteosarcoma, osteoarthritis and rickets.

The compounds according to the invention are suitable for the preparation of a medicament for the treatment of diseases which are caused, mediated and/or propagated by Raf kinases, where the Raf kinase is selected from the group consisting of A-Raf, B-Raf and Raf-1.

Preference is given to the use for the treatment of diseases, preferably from the group of the hyperproliferative and non-hyperproliferative diseases.

These are cancerous diseases or non-cancerous diseases.

The non-cancerous diseases are selected from the group consisting of psoriasis, arthritis, inflammation, endometriosis, scarring, benign prostatic hyperplasia, immunological diseases, autoimmune diseases and immunodeficiency diseases.

The cancerous diseases are selected from the group consisting of brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia.

The compounds according to the invention may also be administered at the same time as other well-known therapeutic agents that are selected for their particular usefulness against the condition that is being treated. For example, in the case of bone conditions, combinations that would be favourable include those with antiresorptive bisphosphonates, such as alendronate and risedronate, integrin blockers (as defined further below), such as αvβ3 antagonists, conjugated oestrogens used in hormone replacement therapy, such as Prempro®, Premarin® and Endometrion®; selective oestrogen receptor modulators (SERMs), such as raloxifene, droloxifene, CP-336,156 (Pfizer) and lasofoxifene, cathepsin K inhibitors and ATP proton pump inhibitors.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibiting VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)mu-[diamineplatinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyidaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-Lvalyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl](20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 1'-acetyl-8-(carbamoyloxymethyl)-4-formyl-6-methoxy-14-oxa-1,1-diazatetracyclo(7.4.1.0.0)tetradeca-2,4,6-trien-9-ylacetic acid ester, swainsonine, lometrexol, dexrazoxane, methioninase, 2'-cyano-2'-deoxy-N-4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The invention furthermore relates to the use of the compounds according to the invention for the preparation of a medicament for the treatment of diseases, where the disease is characterised by disturbed angiogenesis. The disease is preferably cancerous diseases.

The disturbed angiogenesis preferably results from disturbed VEGFR-1, VEGFR-2 and/or VEGFR-3 activity.

Particular preference is therefore also given to the use of the compounds according to the invention for the preparation of a medicament for the inhibition of VEGFR-2 activity.

Assays

The compounds according to the invention described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

VEGF Receptor Kinase Assay

VEGF receptor kinase activity is measured by incorporation of radiolabelled phosphate into 4:1 polyglutamic acid/tyrosine substrate (pEY). The phosphorylated pEY product is trapped on a filter membrane and the incorporation of radiolabelled phosphate is quantified by scintillation counting.

Materials

VEGF Receptor Kinase

The intracellular tyrosine kinase domains of human KDR (Terman, B. I. et al. Oncogene (1991) Vol. 6, pp. 1677-1683.) and FIt-1 (Shibuya, M. et al. Oncogene (1990) Vol. 5, pp. 519-524) were cloned as glutathione S-transferase (GST) gene fusion proteins. This was accomplished by cloning the cytoplasmic domain of the KDR kinase as an in frame fusion at the carboxyl terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% of Triton X-100, 10% glycerol, 10 mg/ml each of leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% of Triton X-100, 10% glycerol, 10 mgiml each of leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% of Triton X-100, 50% glycerol, 10 mg/ml each of leupeptin, pepstatin and aprotinin and 1 mM phenylmethylsulfonyl fluoride.

10× Reaction Buffer 200 mM Tris, pH 7.4, 1.0 M NaCl, 50 mM $MnCl_2$, 10 mM DTT and 5 mg/ml of bovine serum albumin [BSA] (Sigma).

Enzyme Dilution Buffer 50 mM Tris, pH 7.4, 0.1 M NaCl, 1 mM DTT, 10% glycerol, 100 mg/ml of BSA.

10× Substrate

750 µg/ml poly(glutamic acid/tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass-fibre 96-well plate.

Method A—Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 1000×g for 1 hour. The supernatant was then passed over a glutathione Sepharose column (Pharmacia) equilibrated with lysis buffer and washed with 5 volumes of the same buffer followed by 5 volumes of wash buffer. Recombinant GST-KDR protein was eluted with wash buffer/10 mM reduced glutathione (Sigma) and dialysed against dialysis buffer.

Method B—VEGF Receptor Kinase Assay

1. Add 5 µl of inhibitor or control to the assay in 50% DMSO.

2. Add 35 µl of reaction mixture containing 5 µl of 10× reaction buffer, 5 µl of 25 mM ATP/10 µCi[$^{33}$P]ATP (Amersham) and 5 µl of 10× substrate.

3. Start the reaction by the addition of 10 µl of KDR (25 nM) in enzyme dilution buffer.

4. Mix and incubate at room temperature for 15 minutes.

5. Stop the reaction by the addition of 50 µl of stop solution.

6. Incubate at 4° C. for 15 minutes.

7. Transfer a 90 µl aliquot to filter plate.

8. Aspirate and wash 3 times with wash solution.

9. Add 30 µl of scintillation cocktail, seal plate and count in a Wallace Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are purchased from Clonetics Corp. Cells are obtained in endothelial growth medium (EGM; Clonetics) and are used for mitogenic assays at passages 3-7.

Culture Plates

NUNCLON 96-well polystyrene tissue culture plates (NUNC #167008).

Assay Medium

Dulbecco's modification of Eagle's medium containing 1 g/ml of glucose (low-glucose DMEM; Mediatech) plus 10% (v/v) foetal bovine serum (Clonetics).

Test Compounds

Working stock solutions of test compounds are diluted serially in 100% dimethyl sulfoxide (DMSO) to 400 times greater than their desired final concentrations. Final dilutions to 1× concentration are made in assay medium immediately prior to addition to cells.

10× Growth Factors

Solutions of human VEGF 165 (500 ng/ml; R&D Systems) and bFGF (10 ng/ml; R&D Systems) are prepared in assay medium.

10×[³H]thymidine

[Methyl-3H]thymidine (20 Ci/mmol; Dupont-NEN) is diluted to 80 µCi/ml in low-glucose DMEM medium.

Cell Wash Medium

Hank's balanced salt solution (Mediatech) containing 1 mg/ml of bovine serum albumin (Boehringer-Mannheim).

Cell Lysis Solution

1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cell growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10× VEGF solution or 10× bFGF solution. Cells are then incubated at 37° C./5% $CO_2$.

Method 4

After 24 hours in the presence of growth factors, 10×[³H] thymidine (10 µl/well) is added.

Method 5

Three days after addition of [³H]thymidine, medium is removed by aspiration, and cells are washed twice with cell wash medium (400 µl/well followed by 200 µl/well). The washed, adherent cells are then solubilised by addition of cell lysis solution (100 µl/well) and warming at 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I are inhibitors of VEGF and are thus suitable for the inhibition of angiogenesis, such as in the treatment of ocular diseases, for example diabetic retinopathy, and for the treatment of carcinomas, for example solid tumours. The present compounds inhibit VEGF-stimulated mitogenesis of human vascular endothelial cells in culture with IC50 values of 0.01-5.0 µM. These compounds also show selectivity over related tyrosine kinases (for example FGFR1 and the Src family; for relationship between Src kinases and VEGFR kinases, see Eliceiri et al., Molecular Cell, Vol. 4, pp. 915-924, December 1999).

The TIE-2 tests can be carried out, for example, analogously to the methods indicated in WO 02/44156.

The assay determines the inhibiting activity of the substances to be tested in the phosphorylation of the substrate poly(Glu, Tyr) by Tie-2 kinase in the presence of radioactive $^{33}$P-ATP. The phosphorylated substrate binds to the surface of a "flashplate" microtitre plate during the incubation time. After removal of the reaction mixture, the microtitre plate is washed a number of times and the radioactivity on its surface is subsequently measured. An inhibiting effect of the substances to be measured results in lower radioactivity compared with an undisturbed enzymatic reaction.

Above and below, all temperatures are indicated in ° C. In the following examples, "conventional work-up" means: water is added if necessary, the pH is adjusted, if necessary, to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M⁺FAB (fast atom bombardment) (M+H)⁺ESI (electrospray ionisation) (M+H)⁺

EXPERIMENTAL PART

The compounds according to the invention can advantageously be obtained by the following synthesis scheme or analogously thereto:

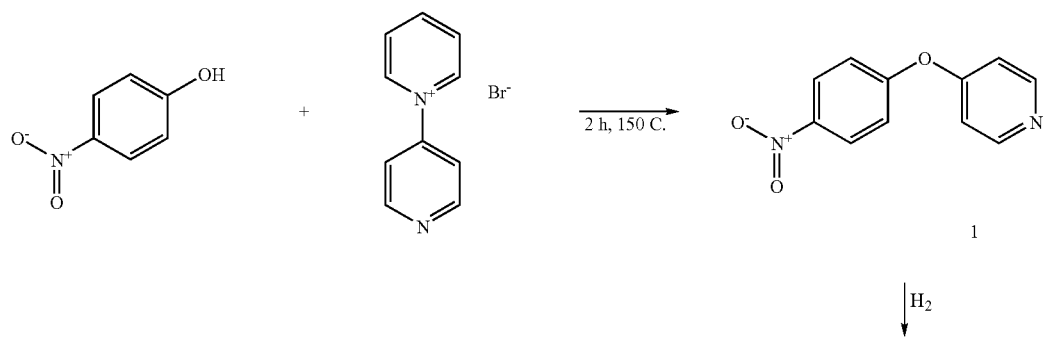

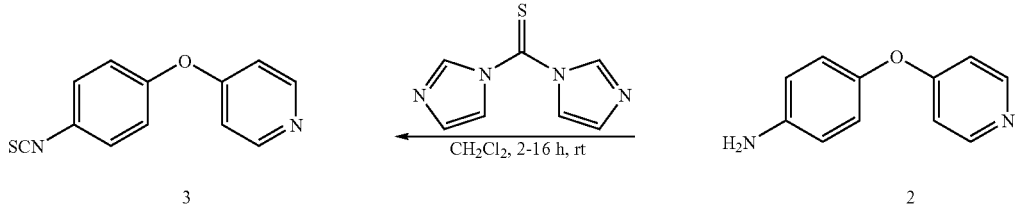

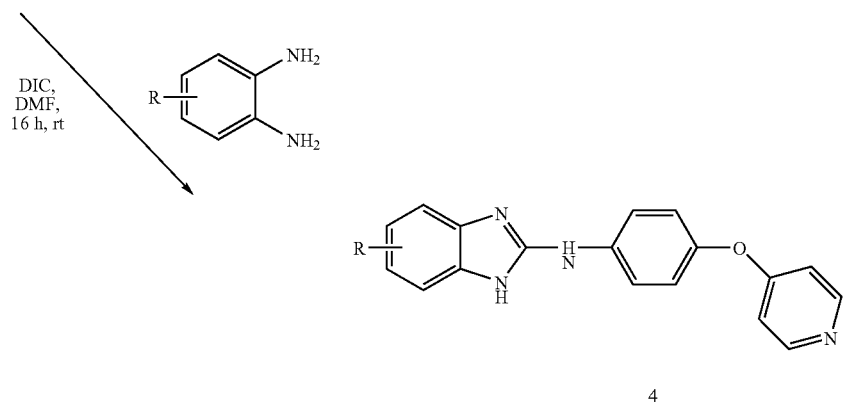

EXAMPLE 1

Synthesis of (6-nitro-1H-benzimidazol-2-yl)[4-(pyridin-4-yloxy)phenyl]amine

1.1 4-(4-Pyridinyloxy)phenylamine (2)

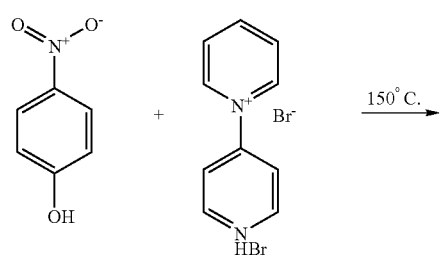

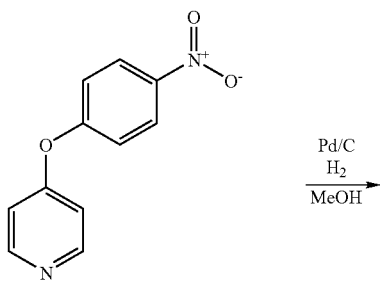

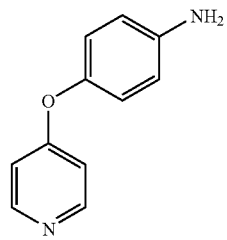

a) 195 g (1.4 mol) of 4-nitrophenol and 445.2 g (1.4 mol) of bipyridine were mixed well and slowly heated to 150° C. After stirring at 150° C. for 2 h, the batch was poured, while still hot, into 5 l of ice-water. The mixture was acidified using hydrochloric acid, and the aqueous phase was washed 2× with 3 l of methyl tert-butyl ether. The aqueous phase was rendered basic (pH 12) using conc. sodium hydroxide solution and extracted 2× with 3 l of methyl tert-butyl ether. The combined organic phases were washed 4× with 1 l of water, dried using $Na_2SO_4$, filtered and evaporated. The residue was dissolved in 100 ml of ether, and the product was brought to crystallisation in an ice bath by addition of 200 ml of petroleum ether. The crystals were filtered off with suction and dried under reduced pressure.

Yield: 75 g (25%) of 1, brown crystals b) Compound I was hydrogenated at room temperature using Pd/C in MeOH. The reaction solution was filtered through kieselguhr, rinsed with MeOH, and the filtrate was subsequently evaporated. The residue was digested with diethyl ether:petroleum ether=2:1, filtered off with suction, rinsed with petroleum ether and dried overnight at 40° C. under reduced pressure.

Yield: 50.94 g (76%) of 2, brown crystals 1.2 4-(4-Pyridinyloxy)phenyl thioisocyanate (3)

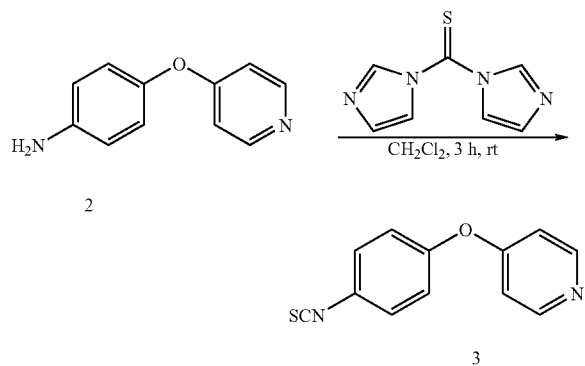

921 mg (4.944 mmol) and 881 mg (4.944 mmol) of 1,1'-thiocarbonyldiimidazole are dissolved in 25 ml of dichloromethane and stirred at room temperature for three hours. The solvent is removed under reduced pressure, and the resultant residue is purified by chromatography over silica gel 60 using ethyl acetate/petroleum ether 4:1 as eluent. Removal of the solvent under reduced pressure gives 915 mg of yellow, crystalline residue 3.

1.3 (6-Nitro-1H-benzimidazol-2-yl)[4-(pyridin-4-yloxy)phenyl]amine (4)

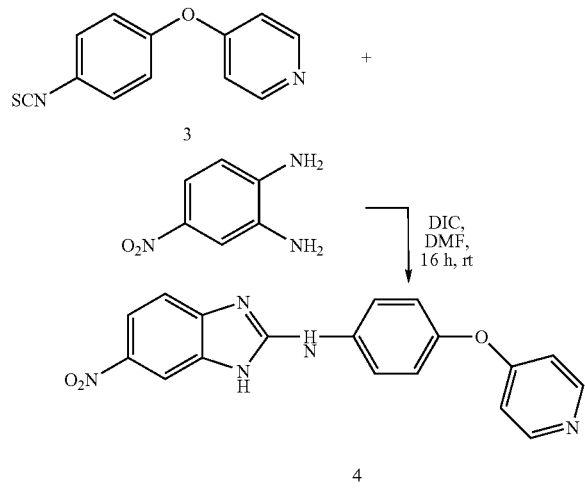

For further reaction, 1006 mg of 4-nitro-1,2-phenylenediamine and 150 mg of the thioisocyanate 3 prepared are dissolved in 5 ml of dimethylformamide and stirred overnight at room temperature. After removal of the solvent, the residue was purified by MPLC chromatography (Rp 18), giving 126 mg of benzimidazolamine 4.

The compounds according to the invention can be purified by HPLC chromatography, preferably as described below:

Method (a):
Column: Chromolith SpeedROD, 50×4.6 mm$^2$ from Merck
Gradient: 5.5 min, t=0, A:B=90:10, t=5.5 min: A:B=0:100
Flow rate: 2.75 ml/min
Eluent: A: Water+0.1% of trifluoroacetic acid (TFA)
B: Acetonitrile+0.08% of TFA
Wavelength: 220 nm Method (b):
Column: Chromolith SpeedROD, 50×4.6 mm$^2$ from Merck
Gradient: 5.0 min, t=0, A:B=95:5, t=4.4 min: A:B=25:75, t=4.5 min to t=5.0 min: A:B=0:100
Flow rate: 2.75 ml/min
Eluent: A: Water+0.1% trifluoroacetic acid (TFA)
B: Acetonitrile+0.08% of TFA
Wavelength: 220 nm The retention times (Rt) obtained by these methods are indicated below for the compounds and are indicated correspondingly by a superscript letter (a or b).

For purification, a preparative HPLC can alternatively be used with the following conditions:
Column: RP 18 (7 μm) Lichrosorb 250×25
Eluent: A: 98H$_2$O, 2 CH$_3$CN, 0.1% of TFA
B: 10H$_2$O, 90 CH$_3$CN, 0.1% of TFA
UV: 225 nm; Flow rate: 10 ml/min.

The following compounds are obtained analogously by reaction of the aromatic diamine with the corresponding thioisocyanate:
(1) (5-Chloro-6-trifluoromethyl-1H-benzimidazol-2-yl)[4-(pyridin-4-yloxy)phenyl]amine (MW=404.77; Rt=1.87[a])
(2) [4-(Pyridin-4-yloxy)phenyl](6-trifluoromethyl-1H-benzimidazol-2-yl)amine (MW=370.33; Rt=1.39[a])
(3) (6-Methyl-1H-benzimidazol-2-yl)[4-(pyridin-4-yloxy)phenyl]amine (MW=316.36; Rt=0.67[a])
(4) (5-Chloro-4-methyl-1H-benzimidazol-2-yl)[4-(pyridin-4-yloxy)phenyl]amine (MW=350.81; Rt=1.30[a])
(5) (4-Bromo-6-trifluoromethyl-1H-benzimidazol-2-yl)[4-(pyridin-4-yloxy)phenyl]amine (MW=449.23; Rt=2.06[a])
(6) (4-Bromo-6-trifluoromethyl-1H-benzimidazol-2-yl)[4-(pyridin-3-yloxy)phenyl]amine (MW=449.23; Rt=2.35[a])
(7) (5,6-Dimethyl-1H-benzimidazol-2-yl)[4-(pyridin-4-yloxy)phenyl]amine (MW=330.39; Rt=1.13[a])
(8) (5-Chloro-6-trifluoromethyl-1H-benzimidazol-2-yl)[4-(pyridin-3-yloxy)phenyl]amine (MW=404.78; Rt=2.08[a])
(9) (5,6-Dichloro-1H-benzimidazol-2-yl)[4-(pyridin-4-yloxy)phenyl]amine (MW=371.23; Rt=1.51[a])
(10) (5,6-Dichloro-1H-benzimidazol-2-yl)[4-(pyridin-3-yloxy)phenyl]amine (MW=371.23; Rt=1.77[a])
(11) (5-Chloro-1H-benzimidazol-2-yl)[4-(pyridin-4-yloxy)phenyl]amine (MW=336.78; Rt=0.81[a])
(12) (5-Chloro-1H-benzimidazol-2-yl)[4-(pyridin-3-yloxy)phenyl]amine (MW=336.78 Rt=1.39[a])
(13) (4-Methyl-1H-benzimidazol-2-yl)[4-(pyridin-3-yloxy)phenyl]amine (MW=316.36; Rt=1.33[a])
(14) (4-Chloro-6-trifluoromethyl-1H-benzimidazol-2-yl)[4-(pyridin-4-yloxy)phenyl]amine (MW=404.78; Rt=2.01[a])
(15) (4-Chloro-6-trifluoromethyl-1H-benzimidazol-2-yl)[4-(pyridin-3-yloxy)phenyl]amine (MW=404.78; Rt=2.25[a])
(16) (4,5-Dimethyl-1H-benzimidazol-2-yl)[4-(pyridin-4-yloxy)phenyl]amine (MW=330.39; Rt=1.21[a])
(17) (5-Chloro-6-methyl-1H-benzimidazol-2-yl)[4-(pyridin-4-yloxy)phenyl]-amine (MW=350.81; Rt=1.29[a])
(18) (5-Chloro-6-methyl-1H-benzimidazol-2-yl)[4-(pyridin-3-yloxy)phenyl]-amine (MW=350.81; Rt=1.61[a])
(19) (4,6-Bistrifluoromethyl-1H-benzimidazol-2-yl)[4-(pyridin-4-yloxy)phenyl]amine (MW=438.33; Rt=2.24[a])
(20) (4,6-Bistrifluoromethyl-1H-benzimidazol-2-yl)[4-(pyridin-3-yloxy)phenyl]amine (MW=438.33; Rt=2.54[a])
(21) [4-(Pyridin-3-yloxy)phenyl](6-trifluoromethyl-1H-benzimidazol-2-yl)amine (MW=370.33; Rt=1.71[a])

(22) (6-Methyl-1H-benzimidazol-2-yl)[4-(pyridin-3-yloxy) phenyl]amine (MW=316.36; Rt=1.42$^a$)

(23) (4,5-Dimethyl-1H-benzimidazol-2-yl)[4-(pyridin-3-yloxy)phenyl]amine (MW=330.39; Rt=1.55°)

(24) (5-Chloro-4-methyl-1H-benzimidazol-2-yl)[4-(pyridin-3-yloxy)phenyl]-amine (MW=350.81; Rt=1.69$^a$)

(25) (4-Methyl-1H-benzimidazol-2-yl)[4-(pyridin-4-yloxy) phenyl]amine (MW=316.36; Rt=0.75$^a$)

(26) (5,6-Dimethyl-1H-benzimidazol-2-yl)[4-(pyridin-3-yloxy)phenyl]amine (MW=330.39; Rt=1.91$^a$)

(27) (4-Bromo-6-trifluoromethyl-1H-benzimidazol-2-yl)[4-(2,6-dimethylpyrimidin-4-yloxy)phenyl]amine (MW=478.27; Rt=3.09$^b$)

(28) N-Methyl-4-[4-(bromotrifluoromethyl-1H-benzimidazol-2-ylamino)phenoxy]pyridine-2-carboxamide (MW=506.28; Rt=3.52$^b$)

(29) 2-[4-(Pyridin-4-yloxy)phenylamino]-3H-benzimidazole-5-carbonitrile (MW=327.35; Rt=1.97$^b$)

(30) [4-(2-Amino-6-methylpyrimidin-4-yloxy)phenyl](4-bromo-6-trifluoromethyl-1H-benzimidazol-2-yl)amine (MW=479.26; Rt=3.01$^b$)

(31) (4-Chloro-6-trifluoromethyl-1H-benzimidazol-2-yl)[4-(2,6-dimethylpyrimidin-4-yloxy)phenyl]amine (MW=433.82; Rt=3.01$^b$)

(32) [4-(2-Amino-6-methylpyrimidin-4-yloxy)phenyl](4-chloro-6-trifluoromethyl-1H-benzimidazol-2-yl)amine (MW=434.81; Rt=3.01$^b$)

(33) (6-Nitro-1H-benzimidazol-2-yl)[4-(pyridin-4-yloxy) phenyl]amine (MW=347.33; Rt=3.08$^b$)

(34) Methyl 2-[4-(pyridin-4-yloxy)phenylamino]-3H-benzimidazole-5-carboxylate (MW=360.37; Rt=3.16$^b$)

(35) 2-[4-(Pyridin-4-yloxy)phenylamino]-3H-benzimidazole-5-carboxylic acid (MW=346.35; Rt=1.89$^b$)

(36) Methyl 7-methanesulfonyl-2-[4-(pyridin-4-yloxy)phenylamino]-3H-benzimidazole-5-carboxylate (MW=438.46; Rt=2.40)

(37) (4-Fluoro-6-trifluoromethyl-1H-benzimidazol-2-yl)[4-(pyridin-4-yloxy)phenyl]amine (MW=388.32; Rt=2.83$^b$)

(38) [4-(2,6-Dimethylpyrimidin-4-yloxy)phenyl](4-fluoro-6-trifluoromethyl-1H-benzimidazol-2-yl)amine (MW=417.37; Rt=2.88$^b$)

(39) [4-(2-Amino-6-methylpyrimidin-4-yloxy)phenyl](4-fluoro-6-trifluoromethyl-1H-benzimidazol-2-yl)amine (MW=418.35; Rt=2.85$^b$)

(40) N-Methyl-4-{4-[6-(1-thiophen-2-ylmethanoyl)-1H-benzimidazol-2-ylamino]phenoxy}pyridine-2-carboxamide (MW=469.52; Rt=2.93$^b$)

(41) $N^2$-[4-(Pyridin-4-yloxy)phenyl]-3H-benzimidazole-2,5-diamine (MW=317.35; Rt=1.55$^b$)

Pharmacological Test Results

| No. | Inhibition of TIE-2 $IC_{50}$ (mol/l) |
|---|---|
| (3) | 40E–07 |
| (5) | 5E–07 |
| (14) | 9E–07 |

The following examples relate to pharmaceutical compositions:

EXAMPLE A

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. A compound comprising formula I

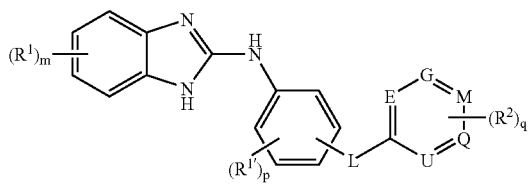

wherein $R^1$, $R^{1'}$, $R^2$ each, independently of one another, are selected from the group consisting of Hal, A, OH, OA, SA, $SO_2H$, $SO_2A$, $SO_3H$, $SO_3A$, CN, $NO_2$, $NH_2$, NHA, NAA', NHCOA, CHO, C(=O)A, COOH, COOA, $CONH_2$, CONHA and CONAA', L is selected from the group consisting of $CH_2$, O and S,

E, G, M,

Q and U each, independently of one another, are selected from the group consisting of a C atom and an N atom, with the proviso that one and no more than one of E, G, M, Q or U is an N atom A, A', independently of one another, are selected from the group consisting of unsubstituted or substituted alkyl having 1-10 C atoms, unsubstituted or substituted cycloalkyl having 3-10 C atoms, unsubstituted or substituted alkoxyalkyl having 2-12 C atoms, unsubstituted or substituted aryl having 6-14 C atoms, unsubstituted or substituted arylalkyl having 7-15 C atoms, Hal is selected from the group consisting of F, Cl, Br and I, and m, p, q each, independently of one another, are 0, 1, 2, 3 or 4, or physiologically acceptable salts, or stereoisomers thereof, including mixtures thereof in all ratios.

2. The compound according to claim 1, wherein
$R^1$, independently of one another, is selected from the group consisting of A, Hal, CN, COOH, COOA, $SO_2$ A, C(=O)A, $NH_2$, NHA and $NO_2$, and
m is 1, 2 or 3,
or physiologically acceptable salts, or stereoisomers thereof, including mixtures thereof in all ratios.

3. The compound according to claim 1 wherein
$R^1$, independently of one another, is selected from the group consisting of methyl, ethyl, $CF_3$, $OCF_3$, F, Cl, Br, CN, COOH, $COOCH_3$, $COOCH_2$ $CH_3$, $SO_2$ $CH_3$, $NH_2$, $NHCH_3$, $NHCH_2$ $CH_3$, $NO_2$, and thiophen-2-ylcarbonyl, and
m is 1, 2 or 3,
or physiologically acceptable salts, or stereoisomers thereof, including mixtures thereof in all ratios.

4. The compound according to claim 1 wherein
$R^{1'}$ is Hal or A,
p is 0 or 1,
or physiologically acceptable salts, or stereoisomers thereof, including mixtures thereof in all ratios.

5. The compound according to claim 1 wherein
$R^2$ is selected from the group consisting of A, COOA, CONHA and $CONH_2$, and
q is 0, 1 or 2,
or physiologically acceptable salts, or stereoisomers thereof, including mixtures thereof in all ratios.

6. The compound according to claim 1 wherein
$R^1$, independently of one another, is selected from the group consisting of Hal, alkyl, CN, COOH, COOalkyl, $SO_2$alkyl, $NH_2$, NHalkyl, C(=O)alkyl, C(=O)heterocyclyl and $NO_2$,
m is 1, 2 or 3
$R^{1'}$ is Hal or A
p is 0 or 1,
L is selected from the group consisting of O, S and $CH_2$,
$R^2$ is selected from the group consisting of A, COOalkyl, CONHalkyl and $CONE_2$, and
q is 0,1 or 2,
or physiologically acceptable salts, or stereoisomers thereof, including mixtures thereof in all ratios.

7. The compound according to claim 1 wherein the group

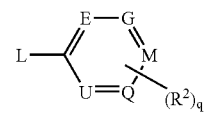

in formula I is selected from the group consisting of

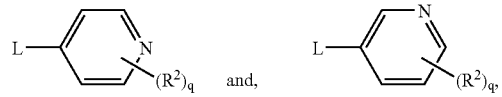

wherein L, $R^2$ and q have the meanings indicated in claim 1, or physiologically acceptable salts, or stereoisomers thereof, including mixtures thereof in all ratios.

8. The compound according to claim 1, selected from the group consisting of
(5-chloro-6-trifluoromethyl-1H-benzimidazol-2-yl)[4-(pyridin-4-yloxy) phenyl]amine;
[4-(pyridin-4-yloxy)phenyl](6-trifluoromethyl-1H-benzimidazol-2-yl)a mine;
(6-methyl-1H-benzimidazol-2-yl)[4-(pyridin-4-yloxy) phenyl]amine;
(5-chloro-4-methyl-1H-benzimidazol-2-yl)[4-(pyridin-4-yloxy)phenyl]a mine;
(4-bromo-6-trifluoromethyl-1H-benzimidazol-2-yl)[4-(pyridin-4-yloxy) phenyl]ainine;
(4-bromo-6-trifluoromethyl-1H-benzimidazol-2-yl)[4-(pyridin-3-yloxy) phenyl]amine;
(5,6-dimethyl-1H-benzimidazol-2-yl)[4-(pyridin-4-yloxy)phenyl]amine;
(5-chloro-6-trifluoromethyl-1H-benzimidazol-2-yl)[4-(pyridin-3-yloxy) phenyl]amine;
(5,6-dichloro-1H-benzimidazol-2-yl)[4-(pyridin-4-yloxy) phenyl]amine;
(5,6-dichloro-1H-benzimidazol-2-yl)[4-(pyridin-3-yloxy) phenyl]amine;
(5-chloro-1H-benzimidazol-2-yl)[4-(pyridin-4-yloxy) phenyl]amine;
(5-chloro-1H-benzimidazol-2-yl)[4-(pyridin-3-yloxy) phenyl]amine;

(4-methyl-1H-benzimidazol-2-yl)[4-(pyridin-3-yloxy) phenyl]amine;
(4-chloro-6-trifluoromethyl-1H-benzimidazol-2-yl)[4-(pyridin-4-yloxy) phenyl]amine;
(4-chloro-6-trifluoromethyl-1H-benzimidazol-2-yl)[4-(pyridin-3-yloxy) phenyl]amine;
(4,5-dimethyl-1H-benzimidazol-2-yl)[4-(pyridin-4-yloxy)phenyl]amine;
(5-chloro-6-methyl-1H-benzimidazol-2-yl)[4-(pyridin-4-yloxy)phenyl]a mine;
(5-chloro-6-methyl-1H-benzimidazol-2-yl)[4-(pyridin-3-yloxy)phenyl]a mine;
(4,6-bistrifluoromethyl-1H-benzimidazol-2-yl)[4-(pyridin-4-yloxy)phen yl]amine;
(4,6-bistrifluoromethyl-1H-benzimidazol-2-yl)[4-(pyridin-3-yloxy)phen yl]amine;
[4-(pyridin-3-yloxy)phenyl](6-trifluoromethyl-1H-benzimidazol-2-yl)a mine;
(6-methyl-1H-benzimidazol-2-yl)[4-(pyridin-3-yloxy) phenyl]amine;
(4,5-dimethyl-1H-benzimidazol-2-yl)[4-(pyridin-3-yloxy)phenyl]amine;
(5-chloro-4-methyl-1H-benzimidazol-2-yl)[4-(pyridin-3-yloxy)phenyl]a mine;
(4-methyl-1H-benzimidazol-2-yl)[4-(pyridin-4-yloxy) phenyl]amine;
(5,6-dimethyl-1H-benzimidazol-2-yl)[4-(pyridin-3-yloxy)phenyl]amine;
N-methyl-4-[4-(bromotrifluoromethyl-1H-benzimidazol-2-ylamino)phe noxy]pyridine-2-carboxamide;
2-[4-(pyridin-4-yloxy)phenylamino]-3H-benzimidazole-5-carbonitrile;
(6-nitro-1H-benzimidazol-2-yl)[4-(pyridin-4-yloxy)phenyl]amine;
methyl 2-[4-(pyridin-4-yloxy) -phenylamino]-3H-benzimidazole-5-carboxylate;
2-[4-(pyridin-4-yloxy)phenylamino]-3H-benzimidazole-5-carboxylic acid;
methyl 7-methanesulfonyl-2-[4-(pyridin-4-yloxy)phenylamino]-3H-benzimidaz ole-5-carboxylate;
(4-fluoro-6-trifluoromethyl-1H-benzimidazol-2-yl)[4-(pyridin-4-yloxy) phenyl]amine;
N-methyl-4-{4-[6-(1-thiophen-2-ylmethanoyl)-1H-benzimidazol-2-yl-amino]phenoxy}pyridine-2-carboxamide;
$N^2$-[4-(pyridin-4-yloxy)phenyl]-3H-benzimidazole-2,5-diamine;
physiologically acceptable salts, and stereoisomers thereof, including mixtures thereof in all ratios.

9. A process for the preparation of a compound according to claim 1 or physiologically acceptable salts, or stereoisomers thereof, including mixtures thereof in all ratios, comprising reacting
a compound of formula II

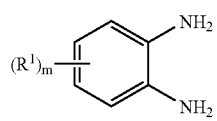

wherein $R^1$ and m have the meanings indicated in claim 1, with a compound of formula III

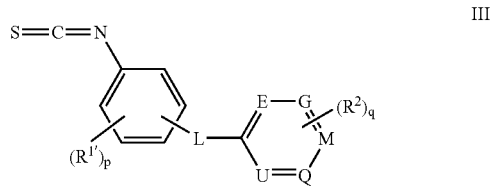

wherein $R^{1'}$, L, B, G, M, Q, U, $R^2$ and q have the meanings indicated in claim 1,
and optionally converting the compound of formula I into a salt.

10. A pharmaceutical composition comprising at least one compound according to claim 1 or physiologically acceptable salts, or stereoisomers thereof, including mixtures thereof in all ratios or optionally excipients or adjuvants.

11. The pharmaceutical composition according to claim 10 comprising at least one additional active ingredient.

12. A kit comprising separate packs of
(a) an effective amount of a compound according to claim 1 or pharmaceutically usable derivatives, and stereoisomers thereof, including mixtures thereof in all ratios, and
(b) an effective amount of an additional active ingredient.

13. A compound comprising formula I

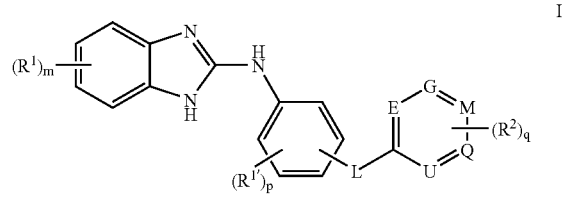

wherein
$R^1$, $R^{1'}$ each, independently of one another, are selected from the group consisting of Hal, A, OH, OA, SA, $SO_2H$, $SO_2A$, $SO_3H$, $SO_3A$, CN, $NO_2$, $NH_2$, NHA, NAA', NHCOA, CHO, C(=O)A, COOH, COOA, $CONH_2$, CONHA and CONAA', wherein A, A' independently of one another, are selected from the group consisting of unsubstituted or substituted alkyl having 1-10 C atoms, unsubstituted or substituted cycloalkyl having 3-10 C atoms, unsubstituted or substituted alkoxyalkyl having 2-12 C atoms, unsubstituted or substituted aryl having 6-14 C atoms, unsubstituted or substituted arylalkyl having 7-15 C atoms,
$R^2$ is selected from the group consisting of Hal, A, OH, OA, SA, $SO_2H$, $SO_2A$, $SO_3H$, $SO_3A$, CN, $NO_2$, $NH_2$, NHA, NAA', NHCOA, CHO, C(=O)A, COOH, COOA, $CONH_2$, CONHA and CONAA', wherein A, A' independently of one another, are selected from the group consisting of unsubstituted or substituted alkyl having 1-10 C atoms, unsubstituted or substituted cycloalkyl having 3-10 C atoms, unsubstituted or substituted alkoxyalkyl having 2-12 C atoms, unsubstituted or substituted aryl having 6-14 C atoms, unsubstituted or substituted arylalkyl having 7-15 C atoms, unsubstituted or substituted, saturated, unsaturated or aromatic heterocyclyl having 2-7 C atoms and 1-3 hetero atoms selected from the group consisting of N, O and S, or unsubstituted or substituted, saturated, unsaturated or aromatic heterocyclylalkyl having 3-10 C atoms and 1-3 hetero atoms selected from consisting of N, O and S, L is selected from the group consisting of $CH_2$, O, and S,

E, G, M,

Q and U each, independently of one another, are selected from the group consisting of a C atom and a N atom, with the proviso that one and no more than one of E, G, M, Q or U is an N atom, Hal is selected from the group consisting of F, Cl, Br and I, and m, p, q each, independently of one another, are 0, 1, 2, 3 or 4, or physiologically acceptable salts, or stereoisomers thereof, including mixtures thereof in all ratios.

\* \* \* \* \*